US 7,780,970 B2

(12) United States Patent
Schlothauer et al.

(10) Patent No.: US 7,780,970 B2
(45) Date of Patent: Aug. 24, 2010

(54) COMPOSITION

(75) Inventors: Ralf-Christian Schlothauer, Te Aroha (NZ); Andrew John Morgan, West Sussex (GB); Inez Rademacher, Tarp (DE); Tove Martel Ida Elsa Christensen, Allerød (DK)

(73) Assignee: Danisco A/S, Copenhagen (DK)

( * ) Notice: Subject to any disclaimer, the term of this patent is extended or adjusted under 35 U.S.C. 154(b) by 1021 days.

(21) Appl. No.: 10/521,097

(22) PCT Filed: Aug. 6, 2003

(86) PCT No.: PCT/GB03/03436
§ 371 (c)(1),
(2), (4) Date: Nov. 4, 2005

(87) PCT Pub. No.: WO2004/013343
PCT Pub. Date: Feb. 12, 2004

(65) Prior Publication Data
US 2006/0057704 A1    Mar. 16, 2006

Related U.S. Application Data

(60) Provisional application No. 60/413,727, filed on Sep. 26, 2002.

(30) Foreign Application Priority Data
Aug. 6, 2002    (GB) ................................ 0218241.8

(51) Int. Cl.
    A61K 45/00    (2006.01)
    A61K 38/43    (2006.01)
    A61K 39/02    (2006.01)
    A01N 63/00    (2006.01)

(52) U.S. Cl. .............. 424/282.1; 424/278.1; 424/93.45; 424/94.1; 424/234.1

(58) Field of Classification Search ................ None
    See application file for complete search history.

(56) References Cited

U.S. PATENT DOCUMENTS 4,444,793 A    4/1984    Schwartz et al.
5,565,342 A    10/1996   Yoneta et al.

FOREIGN PATENT DOCUMENTS

EE    0 790 003 A1    8/1997
EP    0 790 003 A     8/1997
EP    0 881 283 A1    12/1998
EP    0 957 170 A1    11/1999
WO    WO 94/12656    *  6/1994
WO    WO 00/47727 A   8/2000
WO    WO 01/57234     8/2001
WO    WO 02/37984 A1  5/2002
WO    WO 03/008618    1/2003

OTHER PUBLICATIONS

Pailin et al. (Letters in Applied Microbiology, 2001; 33: 45-49).*
Geel-Schutten et al. (Appl Microbiol Biotechnol, 1998; 50: 697-703).*
Applied Microbiology and Biotechnology, vol. 50,, No. 6, 1998, XP002260931, pp. 697-703, Van Geel-Schutten et al., "Screeing and characterization of Lactobacillus strains producing large amounts of exopolysaccharides", Germany.
Applied and Environmental Microbiology, vol. 65, 1999, XP002191551, pp. 53-72, Van Geel-Schutten et al., "Biochemical and structural characterization of the glucan and fructan exopolysaccharides synthesized by *Lactobacillus reuteri* wild-type and mutant strains", Washington, DC.
Applied and Environmental Microbiology, vol. 65, 1999, XP002264246, pp. 73-95, Van Hijum et al., "Molecular characterization of a novel fructosyltransferase from *Lactobacillus reuteri* synthesizing a high molecular weight fructan with beta-(2->1) linked frunctosyl units in *Escherichia coli*", Washington, DC.
Database WPI, Section Ch, Week 200065, Jan. 2000, XP002274658, London, GB.
Faseb Journal, vol. 11, No. 9, 1997, XP001160862, p. A1420, Zahnley et al., "Glycosyltransferase profiles of representative strains of *Leuconostoc mesenteroides*", San Francisco, CA.
Carbohydrate Research, vol. 239, 1993, pp. 209-226, M. Gurter et al., "Structural characterization of the exopolysaccharide produced by *Lactobacillus delbruckii* subspecies bulgaricus rr grown in skimmed milk".
Cerning et al., "Carbon Source Requirements for Exopolysaccharide Production by *Lactobacillus casei* CG11 and Partial Structure Analysis of the Polymer," *Applied and Environmental Microbiology*, vol. 60, No. 11, p. 3914-3919 (Nov. 1994).

* cited by examiner

*Primary Examiner*—Robert B Mondesi
*Assistant Examiner*—Lakia J Tongue
(74) *Attorney, Agent, or Firm*—Steptoe & Johnson LLP

(57) ABSTRACT

The present invention relates to a composition and a method of preparing or treating food products so as to improve their aroma, flavor, mildness, sweetness, consistency, texture, body, mouth feel, firmness, viscosity, gel fracture, wheying off, structure and/or organoleptic properties, nutrition and/or health benefits. In particular, the present invention provides a composition comprising a live micro-organism, an enzyme produced by said micro-organism and an exopolysaccharide (EPS) produced by the activity of said enzyme.

27 Claims, 20 Drawing Sheets

Evaluation of best strain for exopolysaccharide (EPS) production.

Figure 2:
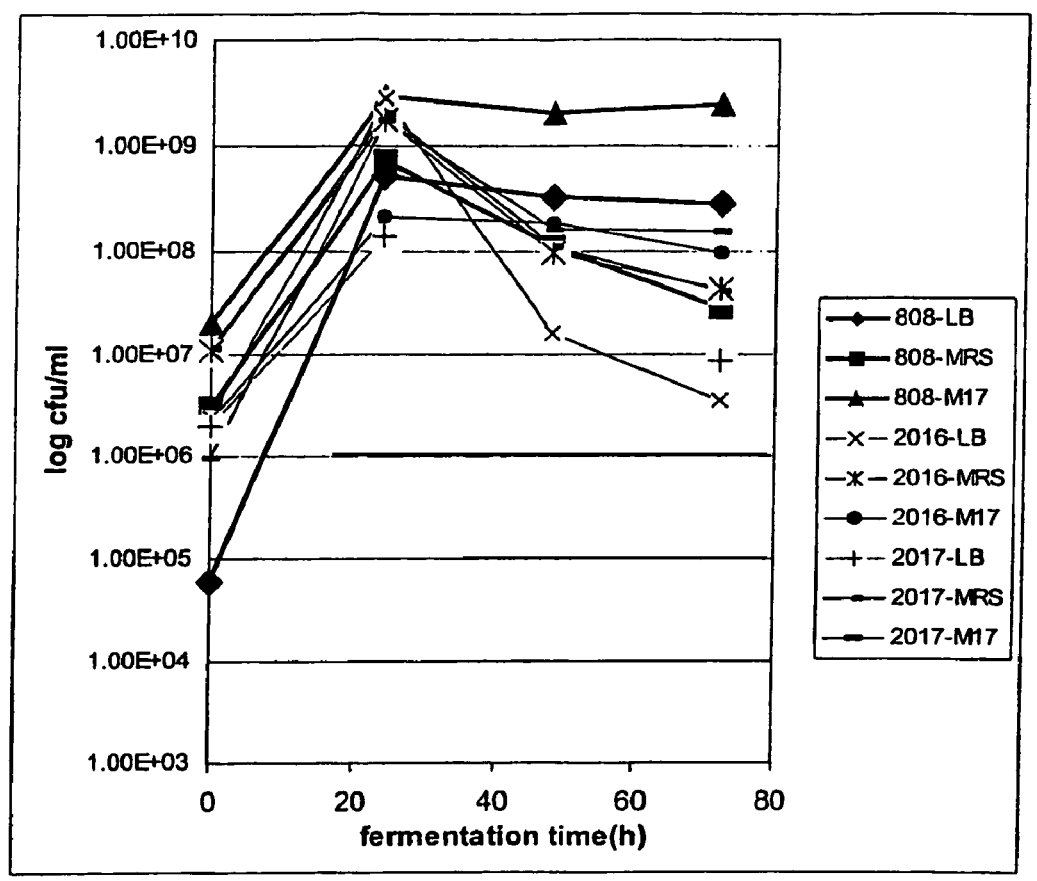

Figure 2. Evaluation of cell count of EPS producing strains

Evaluation of best temperature for EPS production using *Leuconostoc mesonteroides* 808

Evaluation of EPS production and viscosity increase using *Leuconostoc mesonteroides* 808

Evaluation of EPS production as a function of a varied sucrose concentration using *Leuconostoc mesonteroides* 808.

Evaluation of EPS production and viscosity increase as a function of a varied sucrose concentration using *Leuconostoc mesonteroides* 808

EPS production by *Leuconostoc mesenteroides* 121, 808, 1299B strains in growth medium supplemented with different amounts of sucrose/maltose.

**Changes in viscosity produced by *Leuconostoc mesenteroides* 808 strain in growth medium supplemented with different amounts of sucrose/maltose.** Numbers 61 and 62 represent sucrose/maltose ratio 2.5% / 7.5%, number 63 represents 10% sucrose, numbers 64, 65, 67 and 68 represent sucrose/maltose ratio 5% / 5%, numbers 66 and 69 represent sucrose/maltose ratio 7.5% / 2.5%.

Figure 8. EPS production by *Lactobacillus sakei* 570 strain in sucrose/maltose and lactose supplemented growth medium.
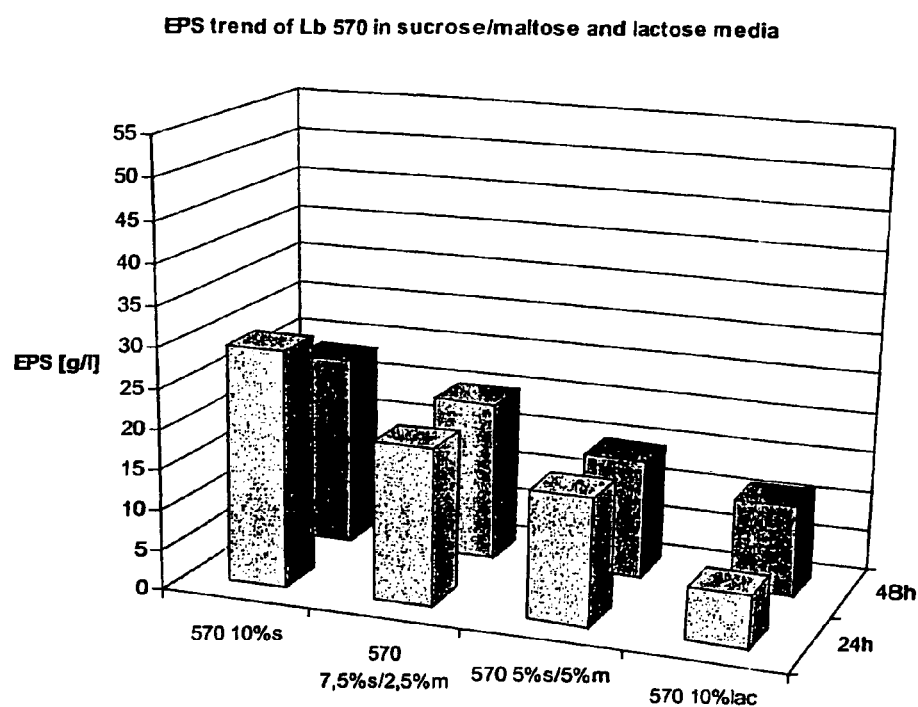

Figure 9. EPS production by *Lactobacillus plantarum* 853 strain in sucrose/maltose and lactose supplemented growth medium.
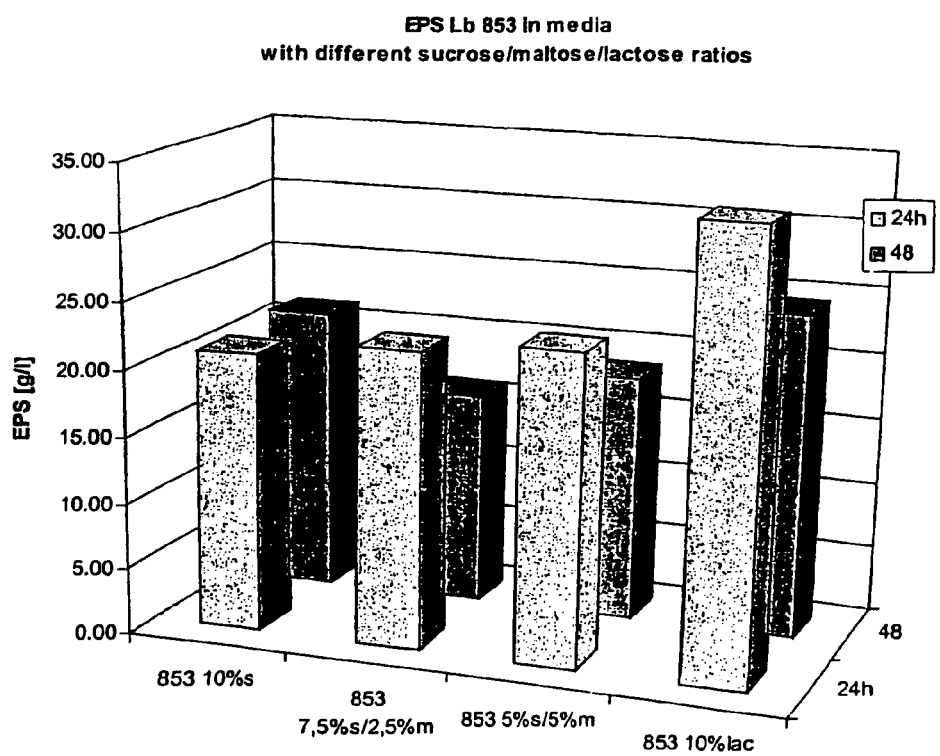

Figure 10. EPS production by *Lactobacillus salivarius* 1502 strain in sucrose/maltose and lactose supplemented growth medium.
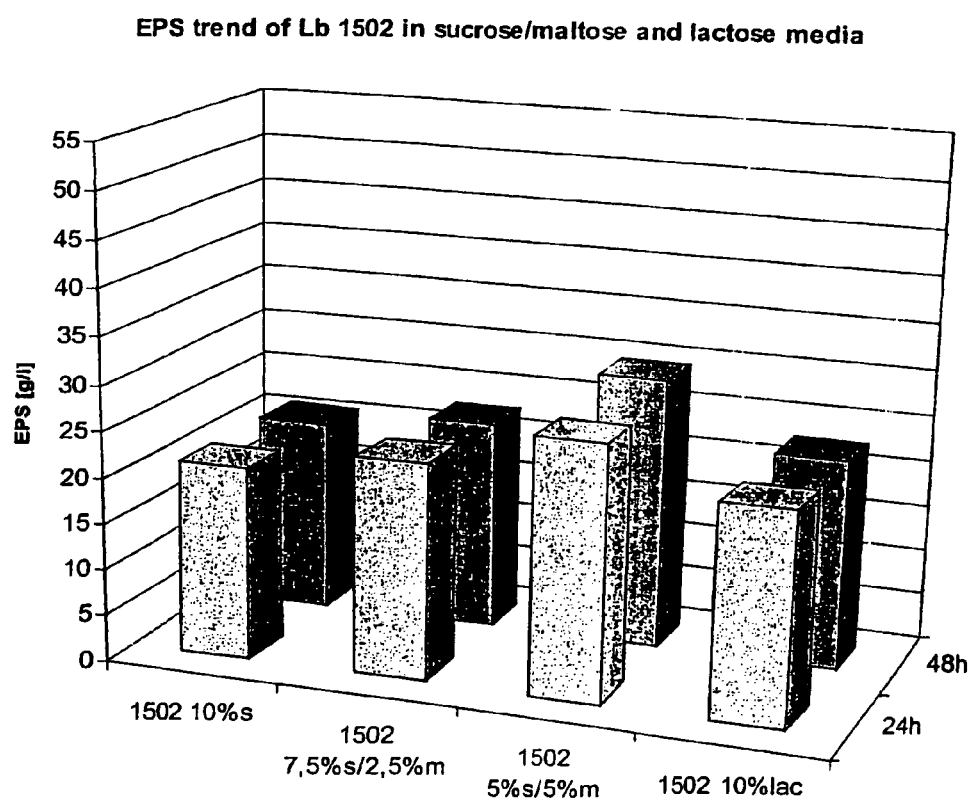

Figure 11.

Ln 808, Lb 570, Lb 853, Lb 1502 , Effect of maltose an the EPS strain length; production of oligosaccharides, EPS production from Lactose 25°C       48h (sample to DK, EPS) / 72h (pH, cfu/ml)

| strain | Medium | time [h] | Temp. [°C] | Sugar Sucrose | Maltose | EPS [g/l] | GKZ start | finish | pH start | finish |
|---|---|---|---|---|---|---|---|---|---|---|
| 808 | Lactic x | 48 / 72 | 25 | 100 | - | 50 | 5,00E+07 | 2,00E+08 | 6,6 | 4,7 |
|  | Lactic x |  |  | 75 | 25 | 30 | 4,00E+06 | 6,00E+08 | 6,8 | 4,4 |
|  | Lactic x |  |  | 50 | 50 | 16 | 5,00E+06 | 5,00E+08 | 6,8 | 4,4 |
| 570 | MRS x | 48 / 72 | 25 | 100 | - | 20 | 2,00E+06 | 3,00E+07 | 6,5 | 4,4 |
|  | MRS x |  |  | 75 | 25 | 18 | 1,00E+06 | 8,00E+07 | 6,5 | 4,4 |
|  | MRS x |  |  | 50 | 50 | 12 | 2,00E+06 | 4,00E+07 | 6,5 | 4,4 |
|  | MRS 100 Lac |  |  | - | - | 11 | 2,00E+06 | 2,00E+08 | 6,5 | 5,8 |
| 853 | MRS x | 48 | 25 | 100 | - | 20 | 2,00E+05 | 8,00E+08 | 6,9 | 5,1 |
|  | MRS x |  |  | 75 | 25 | 16 | 3,00E+05 | 2,00E+09 | 6,9 | 4,7 |
|  | MRS x |  |  | 50 | 50 | 18 | 2,00E+05 | 3,00E+09 | 6,9 | 4,6 |
|  | MRS 100 Lac |  |  |  |  | 33 | 1,00E+05 | 1,00E+09 | 6,8 | 4,6 |
| 1502 | MRS x | 48 | 25 | 100 | - | 20 | 2,00E+04 | 2,00E+08 | 6,9 | 4,4 |
|  | MRS x |  |  | 75 | 25 | 24 | 2,00E+04 | 3,00E+08 | 6,9 | 4,4 |
|  | MRS x |  |  | 50 | 50 | 28 | 2,00E+04 | 3,00E+08 | 6,8 | 4,4 |
|  | MRS 100Lac |  |  | - | - | 20 | 2,00E+04 | 2,00E+08 | 6,8 | 4,4 |

Figure 12. EPS production by *Leuconostoc mesenteroides* 808 in sucrose supplemented growth medium at different pH conditions.
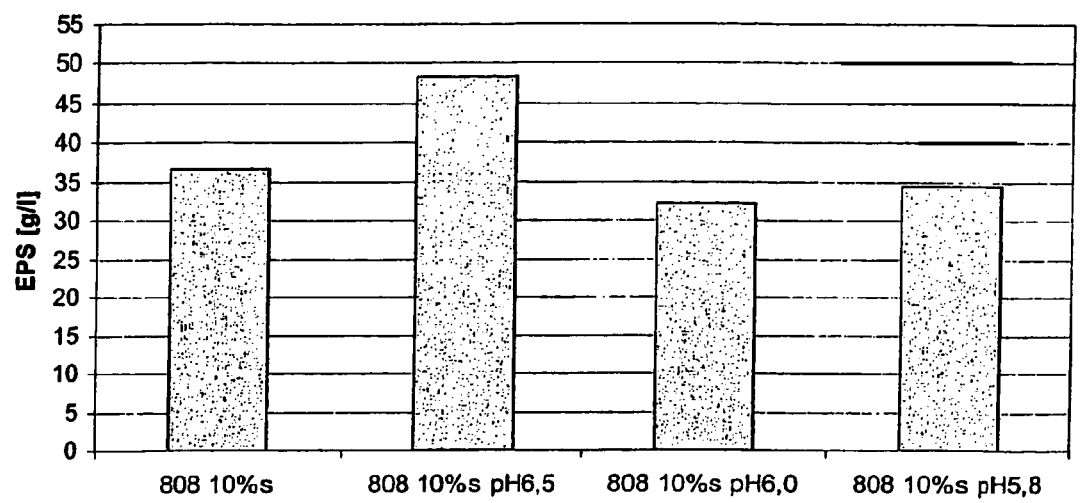

Figure 13. EPS production by *Lactobacillus sakei* 570 in sucrose supplemented growth medium at different pH conditions.
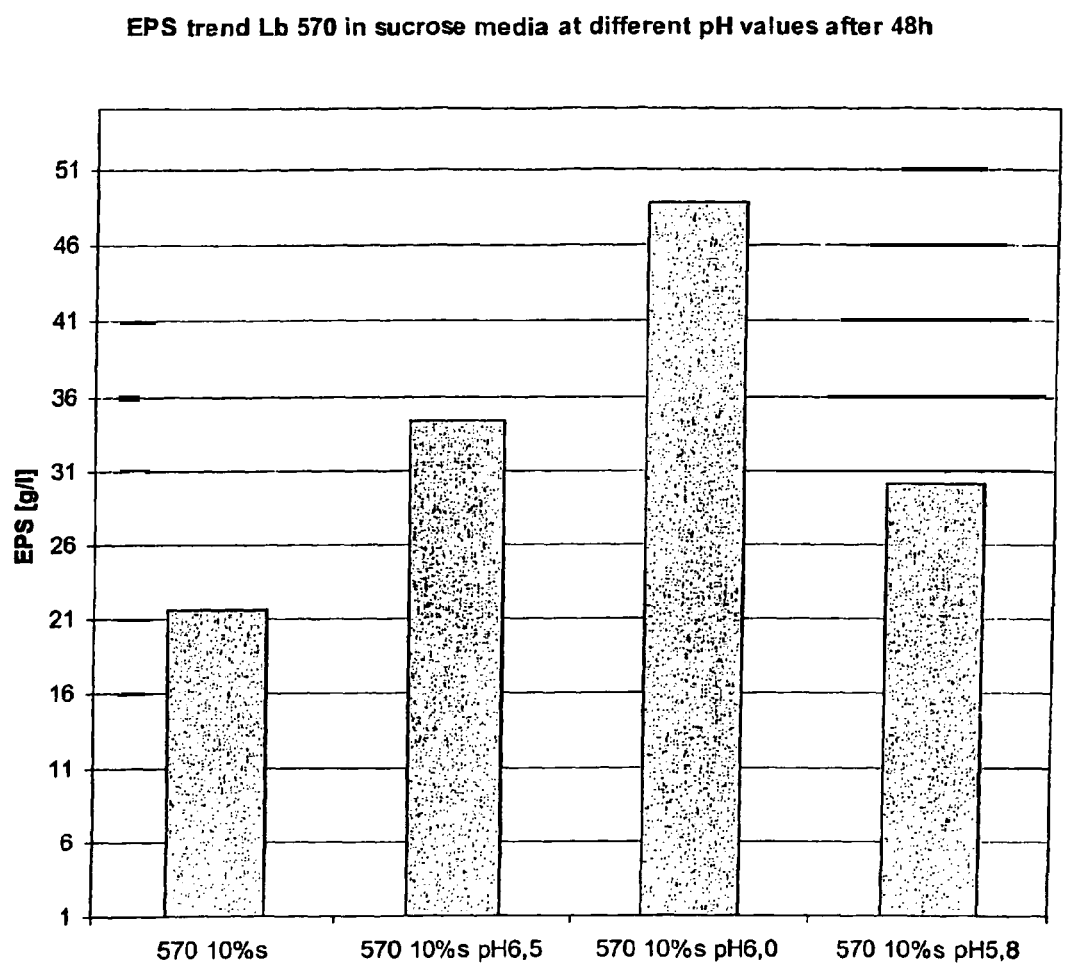

Figure 14. EPS production by *Lactobacillus plantarum* 853 in sucrose supplemented growth medium at different pH conditions
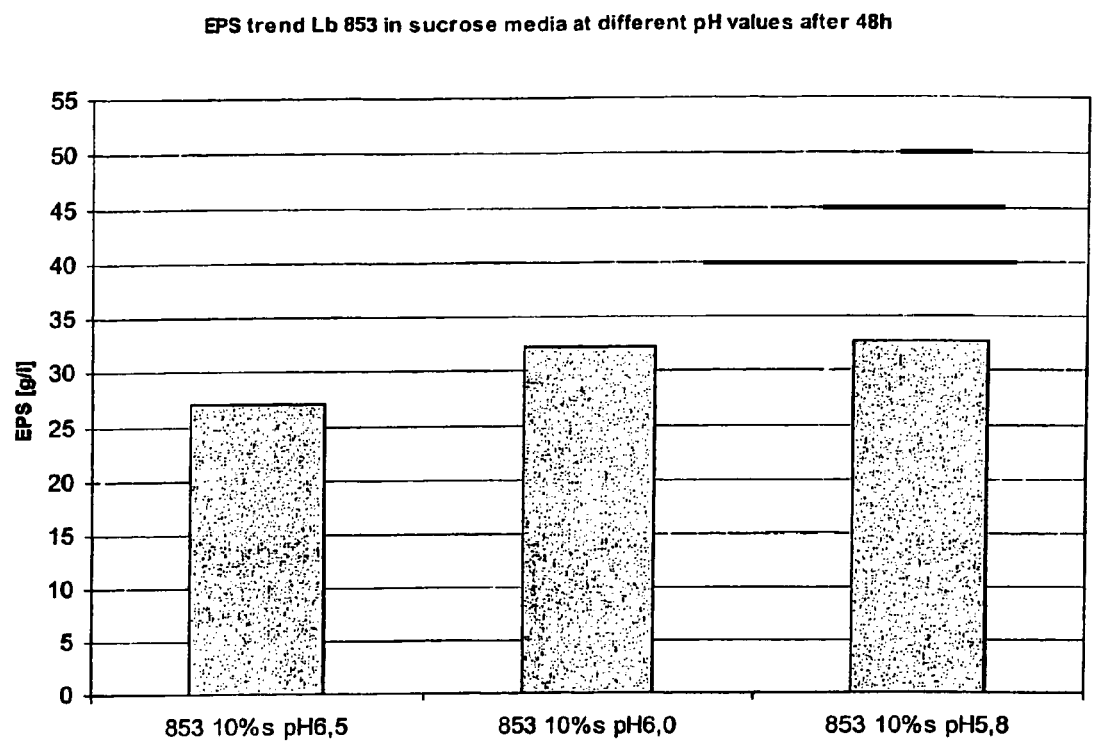

Figure 15. Viscosity of *Leuconostoc mesenteroides* 808 in sucrose supplemented growth medium at different pH conditions.
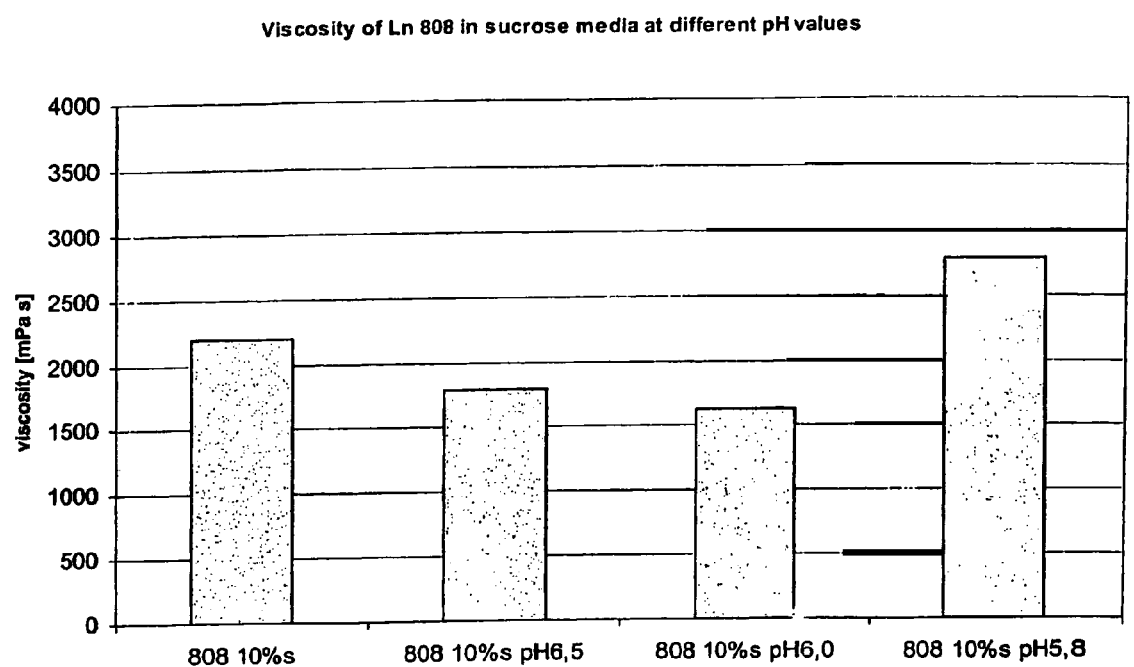

Figure 16. Viscosity of *Lactobacillus sakei* 570 in sucrose supplemented growth medium at different pH conditions.
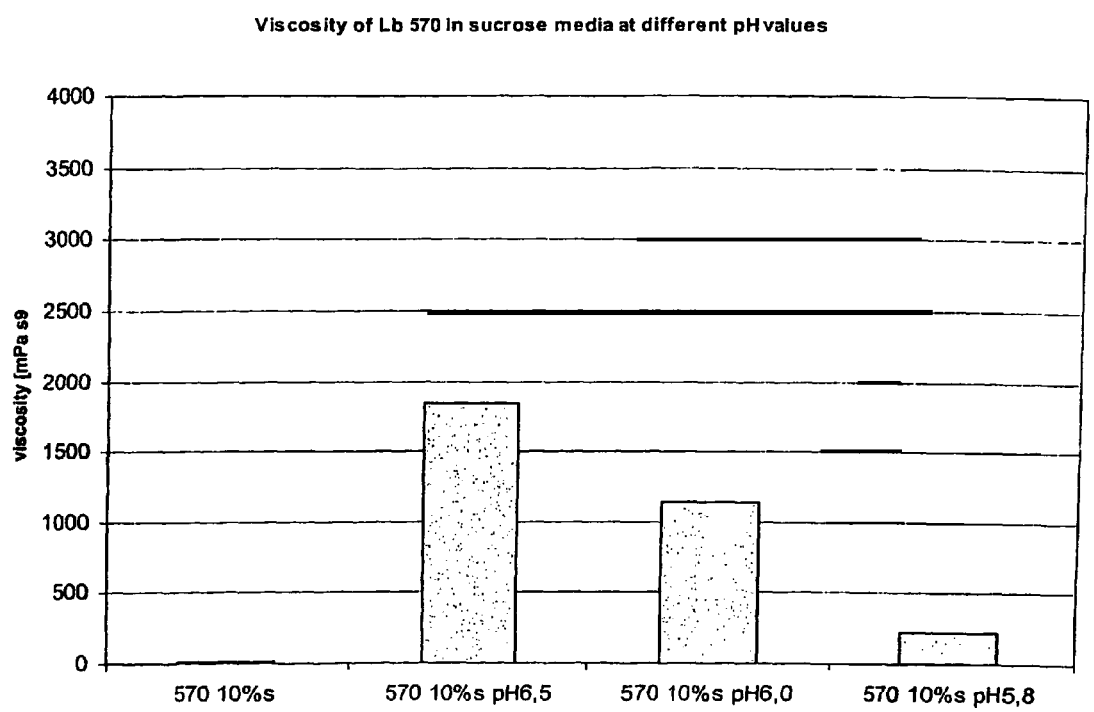

Figure 17. Viscosity of *Lactobacillus plantarum* 853 in sucrose supplemented growth medium at different pH conditions.
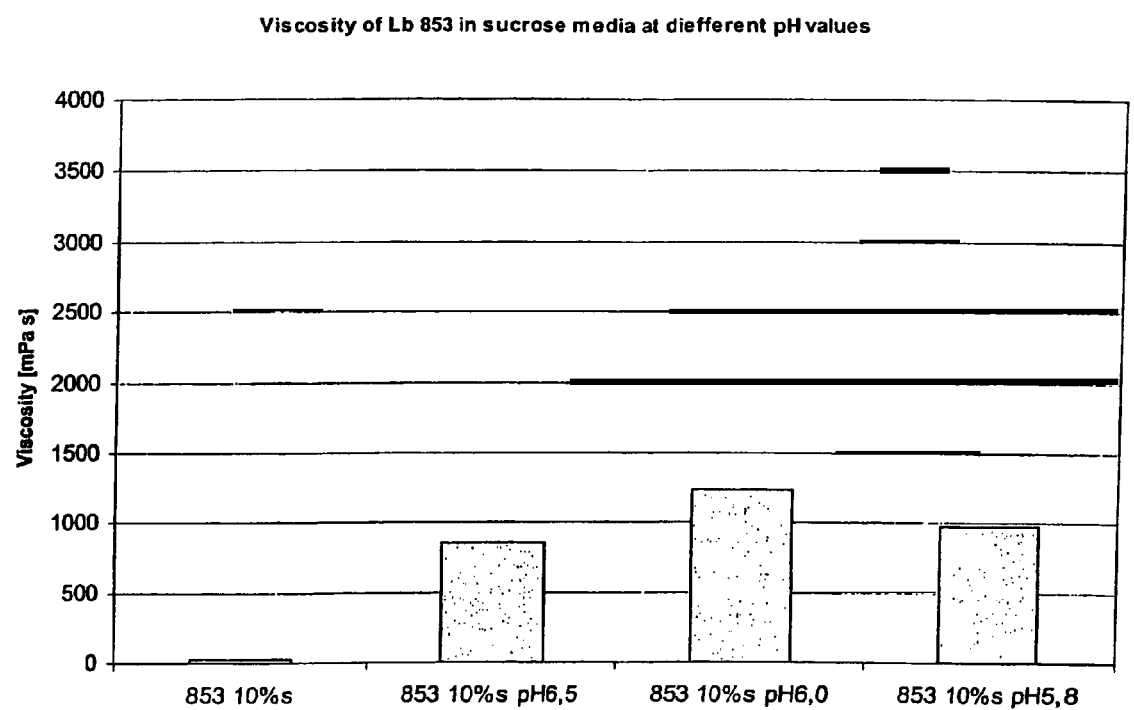

Figure 18. NMR structural analysis of the EPS
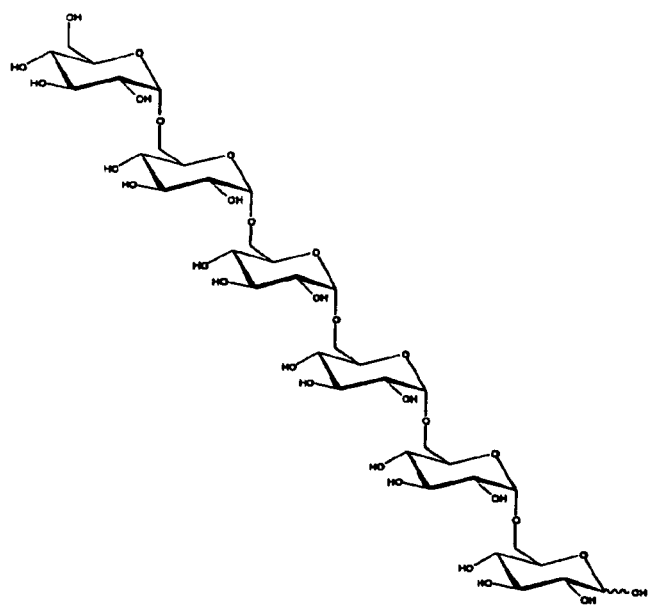
α-D-Glcp-(1→6)-α-D-Glcp-(1→6)-α-D-Glcp-(1→6)-α-D-Glcp-(1→6)-α-D-Glcp-(1→6)-α/β-D-Glcp Figure 19. Spray drying of *Leuconostoc mesonteroides* 808 containing EPS ingredient.

COMPOSITION

This application claims priority under 35 USC 365(c) to International Application No. PCT/GB2003/003436, filed on Aug. 6, 2003, which claims priority to GB Patent Application No. 0218241.8, filed on Aug. 6, 2002, and claims priority under 35 USC §119(e) to U.S. Provisional Application Ser. No. 60/413,727, filed on Sep. 26, 2002, each of which is incorporated by reference in its entirety.

FIELD OF INVENTION

The present invention relates to a composition.

INTRODUCTION

Several useful microbial polysaccharides are currently commercially produced via fermentation processes. These polysaccharides have already found specific applications in diverse fields such as food/feed industry, agro-chemistry, crude-oil recovery, medicine and pharmacology, fine chemistry and cosmetics, separation technology and polymer chemistry. Useful microbial polymers are biodegradable, non-toxic and are formed via fermentation from renewable resources. Many microorganisms (bacteria, fungi, yeasts, micro-algae) produce such polymers, intra-cellularly, extra-cellularly (exo-polysaccharides) or as part of their outer cell wall.

Many lactic acid bacteria (LAB) are able to produce exo-polysaccharides (EPS) (Cerning, 1990, *FEMS Microbiol. Rev.* 87: 113-472). As used herein, the term EPS includes one type of exo-polysaccharide or two or more exo-polysaccharides.

Sometimes, EPS-producing LAB are responsible for undesirable ropiness in food products such as wine (Llauberes et al., 1990, *Carbohydr. Res.* 203: 103-107), and cider (Whiting, 1975, Lactic Acid Bacteria in Beverages and Food, Academic Press, London pp. 69-86). However, in many cases, the polysaccharides released exo-cellularly by LAB may offer advantages in a variety of fermented food products. Indeed, lactic acid bacteria play a pivotal role in the manufacturing of fermented dairy products such as yoghurt, drinking yoghurt, cheese, fermented cream, milk based desserts and others.

There is a large diversity of EPS produced by different LAB in terms of quality, chemical composition, molecular size, charge, presence of side chains and rigidity of the molecules. EPS can act both as texture improvers and stabilisers, firstly by increasing the viscosity and elasticity of the final product, and secondly by binding hydration water and interacting with other milk constituents, such as proteins and micelles, to strengthen the rigidity of the casein network. As a consequence, EPS can decrease syneresis (serum separation) and improve product stability.

The microflora of the large intestine comprises several hundred different bacterial species. This complex community and their metabolic activities have a fundamental effect on the host. Despite the lack of complete understanding of the ecological interactions between the bacteria themselves and the host, experimental data indicate that certain bacteria are believed to benefit the host whereas others may be harmful due to production of toxins and genotoxic metabolites or as a result of mucosal invasion. One approach to positively affect the composition of the intestinal microflora and their metabolic activity is the ingestion of so-called prebiotics. These are defined as non-digestible food ingredients that beneficially affect the host by selectively stimulating the growth and/or activity of one or a number of beneficial bacteria in the gut and thus improve health (Gibson and Roberfroid, 1995, *J. Nutr.* 125: 1401-1412). Potentially health-promoting bacteria are thought to be species of the genera *Lactobacillus* and *Bifidobacterium* (Orrhage and Nord, 2000, *Drugs Exp. Clin. Res.* 26: 95-111).

It has been reported that EPS may affect gut health. It is speculated that the increased viscosity of EPS containing foods may increase the residence time of ingested fermented milk in the gastrointestinal tract and therefore be beneficial to a transient colonisation by probiotic bacteria (German et al., 1999, *Trends in Biotechnology*, 17, 492-499). EPS produced by *Lactobacillus lactis* subsp *cremoris* B40 and *Lactobacillus sakei* 0-1, *S. thermophilus* SFi 20 was shown to be resistant to degradation by faecal microorganisms (Ruijssenaars et al., 2000, *Current Microbiology*, 40, 194-199).

EPS have been suggested to have anti-tumour, cholesterol lowering and immune-modulatory effect (Ode et al., 1983, *Agricultural and Biological Chemistry*, 47:1623-1625; Honoso et al., 1997, *Bioscience. Biotechnology and Biochemistry*, 61: 312-316; Vincent et al., 2001, *Gycobiology*, 11: 131-139).

EPS have been suggested as food ingredients. By way of example, reference can be made to WO 94/12656 wherein a process for producing EPS from a *Lactobacillus sake* like strain is described wherein said EPS has shear-thinning properties and/or thickening and/or emulsion-stabilising properties when added to food products. This process comprises inoculating a medium with an EPS producing strain of bacteria; growing said bacterium under suitable conditions whereby said EPS is formed and isolating said EPS which can then be added as an ingredient to food products wherein said EPS provides shear-thinning, thickening and/or emulsion-stabilising properties to foods containing said EPS.

U.S. Pat. No. 6,004,800 describes a novel *Leuconostoc mesenteroides* ssp. *cremoris* capable of producing dextran sucrase which is capable of converting sucrose into the polysaccharide dextran which in turn is used in texturing and improving the taste of dairy products.

WO 01/57234 describes a natural isolate of *Lactobacillus lactis* ssp. *cremoris* Ropy 352 which contains a plasmid that encodes 13 active genes. The enzymes encoded by these genes permit the bacteria to produce an exopolysaccharide (EPS 352) which is charged, contains 54% to 58% glucose, 42% to 46% galactose and has a molecular weight in the range of 800,000 to 8,000,000. The addition of EPS 352 to milk or other liquids, imparts desirable sensory characteristics to the milk, including making the milk very thick, with a fine and smooth mouth-feel, and a slight sweetness with a "chewable-bite". It is also mentioned that Ropy 352 producing EPS, or EPS 352 alone may be added to any milk-based or non-milk based product, including any liquid food product, to produce the specified sensory characteristics.

Rawson & Marshall, 1997 report that the ropy strains *Lactobacillus delbrueckii* ssp. *bulgaricus* and *Lb. bulgaricus* can improve the 'adhesiveness' of stirred yoghurt products. Although 'adhesiveness' was shown to be due to the effects of the secreted EPS, 'firmness' and 'elasticity' of the stirred yoghurt products were influenced by protein-protein interactions and the protein matrix of the yoghurt (Rawson & Marshall, 1997, *Int. Journal of Food Science and Technology*, 32, 213-220).

Broadbent et al., report that encapcidated, but not ropy, EPS producing *Streptococcus thermophilus* lactic acid bacteria can be used to increase moisture content and improve melt in Mozzarella cheese, without deleteriously affecting whey viscosity (Broadbent et al., 2001, *Int. Dairy J.*, 11, 433-439).

Hess et al., report that yoghurt made with exopolysaccharide producing strains of *Lactobacillus delbrueckii* ssp. *bulgaricus* exhibit less shear thinning than products made with non-EPS producing strains which is consistent with a mechanism for shear-induced structural degradation of yoghurt made using EPS producing strains in which polymer associated with the casein network prevents disruption of portions of the network (Hess et al., 1997, *J. Dairy Sci*, 80, 252-263).

EP 0325872 describes a process for preparing oligodextrans characterised in that sucrose and a sugar acceptor of glucose chosen from a group consisting of maltose, isomaltose, isomaltotriose, methyl α-glucoside and glucose are brought into contact in the presence of glucosyltransferase enzyme extracted from the strain NRRL B-1299 of the lactic acid bacterium *Leuconostoc mesenteroides*. These oligodextrans are then separated from the live culture of *Leuconostoc mesenteroides* and used as fillers in sugar substitutes or as food staff additives having a beneficial effect on the intestinal flora of humans or animals.

WO 01/90319 discloses a novel protein having fructosyl transferase which is capable of catalysing the formation of oligosaccharides or polysaccharides, produced by *Lactobacillus reuteri*. A process for producing said enzyme comprising culturing said *lactobacilli* in a culture medium and recovering said enzyme from culture medium or the cell free extract and using said *lactobacilli* containing said enzyme capable of producing oligosaccharides or polysaccharides as a probiotic or a symbiotic.

Similarly, WO 01/90372 discloses a novel protein having glucosyl transferase activity produced by *Lactobacillus reuteri*. A process for producing said enzyme comprising culturing said *lactobacilli* in a culture medium and recovering said enzyme from culture medium or the cell free extract and using said *lactobacilli* containing said enzyme as a probiotic or a symbiotic.

EP 0881283 discloses a new strain of *Leuconostoc mesenteroides* ssp. *cremoris* capable of producing an enzyme (dextran-sucrase) which can polymerise saccharose and form dextran. This application also discloses a process for producing a composition comprising said enzyme and said dextran for use in the food and cosmetics industry.

Broad Aspects

In a broad aspect, the present invention relates to a composition for consumption. The composition may be for use as a product for consumption or as an ingredient of a product for consumption. In particular, the present invention relates to a composition comprising a viable lactic acid bacterium (LAB), an enzyme synthesised by said lactic acid bacterium and an EPS produced by said enzyme. Thus the present invention relates to a composition and a method of preparing or treating products for consumption so as to improve their aroma, flavour, mildness, sweetness, consistency, texture, body, mouth feel, firmness, viscosity, gel fracture, wheying off, structure and/or organoleptic properties, nutrition and/or health benefits. In particular, the present invention provides a composition comprising a live micro-organism, an enzyme produced by said micro-organism and an EPS produced by the activity of said enzyme.

To date, no one has suggested the use of said composition as a food product or as an ingredient, such as an ingredient for a range of different food products.

Other aspects of the present invention are presented in the accompanying claims and in the following description. These aspects are presented under separate section headings. However, it is to be understood that the teachings under each section are not necessarily limited to the particular section heading.

Specific Aspects

In one aspect, the present invention provides a composition for consumption where the composition comprises a viable lactic acid micro-organism, an enzyme synthesised by said micro-organism and an EPS product of said enzyme.

In another aspect the EPS product is formed in situ by cultivating the lactic acid micro-organism with a suitable enzyme substrate. A suitable enzyme substrate can be any sugar molecule such as a mono-saccharides, di-, tri- or tetrasaccharide. By may of a non-limiting example, mono-saccharides include sugars such as glucose, fructose or galactose while di-saccharides include sugars such as maltose, lactose or sucrose. Other sugar molecules which can be used as a suitable enzyme substrate include the galactoside sugar molecules such as raffinose, stacchyose or verbascose.

In yet another aspect there is provided a composition wherein the enzyme is a glycosyl transferase enzyme (transglycosylase) such as fructosyl transferase enzyme or glucan sucrase capable of polymerising sucrose and/or lactose and/or stacchyose and/or raffinose and/or verbascose.

The present invention further provides a method for preparing a product for consumption—such as a food product or a food ingredient—the method comprising admixing the composition of the present invention with another component so as to form said product for consumption.

The present invention also provides a method for preparing a pharmaceutical product or a pharmaceutical ingredient—the method comprising admixing the composition of the present invention with another component.

In another aspect the present invention relates to the use of a composition comprising a lactic acid micro-organism, an enzyme derived from said lactic acid micro-organism capable of producing an EPS and an EPS produced by said enzyme, wherein said EPS has been produced by said viable micro-organism, for improving the aroma, flavour, sweetness, mildness, consistency, texture, body, mouth feel, firmness, viscosity, gel fracture, wheying off, structure and/or organoleptic properties, nutrition and/or health benefits of said food product according to the present invention.

In yet another aspect the present invention relates to the use of a composition according to the invention wherein said lactic acid bacteria and EPS act as prebiotics when used as ingredients to products for consumption or to pharmaceutical products.

The present invention also relates to a process for in situ producing a composition comprising growing said lactic acid bacteria in a medium (preferably an edible medium) under conditions where enzyme is produced and EPS is formed or until a suitable amount of EPS is formed typically in the order of 2 g-50 g/l, or until a suitable amount of enzyme is formed, and the number of said *lactobacilli* is in a suitable amount—typically in the order of about $10^3$ to about $10^{11}$, preferably about $10^5$ to about $10^{11}$ per ml and more preferably about $10^8$ to about $10^{11}$ per ml.

In a further aspect the present invention provides a method for screening for a suitable composition for use in the present invention, said method comprising contacting a candidate composition with a food product and determining the extent of improvement in texture, body, mouth feel, viscosity, structure and/or organoleptic properties of said food product; wherein said composition comprises a viable micro-organism, and enzyme produced by said micro-organism and an EPS produced by said enzyme.

A further aspect of the present invention relates to use a composition comprising a viable lactic acid micro-organism, enzyme synthesised by said micro-organism and an EPS made up of homopolysaccharide and heteropolysaccharide molecules produced by said enzyme.

Preferred Aspects

In a preferred aspect, the composition for use in the present invention is used in a concentrated form.

Preferably, the composition for use in the present invention is spray-dried, frozen, freeze dried and/or re-suspended or concentrated for example, via a membrane filtration or an evaporation step.

Preferably, the viable micro-organism for use in the present invention is a lactic acid micro-organism which can be selected from a group comprising *Lactococcus, Streptococcus, Pediococcus, Enterococcus, Leuconostoc, Carnobacterium, Propionibacterium, Bifidobacterium* and *Lactobacillus* genuses.

In a preferred aspect the viable micro-organism for use in the present invention is from the genus *Leuconostoc*.

In a preferred aspect the viable micro-organism for use in the present invention is *Leuconostoc mesenteroides*.

In a preferred aspect the viable *Leuconostoc mesenteroides* is capable of producing an enzyme wherein said enzyme is a transglycosylase.

In another preferred aspect the transglycosylase enzyme is a fructosyl transferase or a glycosyl transferase.

In a preferred aspect the *Leuconostoc mesenteroides* produced enzymes is capable of catalysing sucrose and/or lactose into an EPS.

In a preferred aspect the *Leuconostoc mesenteroides* produced enzymes is capable of catalysing raffinose, stacchyose or verbascose into an EPS.

In a preferred aspect the EPS produced by said *Leuconostoc mesenteroides* produced enzyme comprises at least a long chain polymer (polysaccharide) and/or a short chain polymer (oligosaccharide).

In a preferred aspect the polysaccharide or the oligosaccharide components of the EPS comprise fructan and/or glucan.

In a preferred aspect the viable micro-organism for use in the present invention is from the genus *Lactobacillus*.

In a preferred aspect the viable micro-organism for use in the present invention is *Lactobacillus sake* spp., *Lactobacillus plantarum* spp. or *Lactobacillus salivarius* spp.

In a preferred aspect the viable *Lactobacillus sake* spp., *Lactobacillus plantarum* spp. or *Lactobacillus salivarius* spp. are capable of producing an enzyme wherein said enzyme is a glucan sucrase.

In a preferred aspect the *Lactobacillus sake* spp., *Lactobacillus plantarum* spp. or *Lactobacillus salivarius* spp. produced enzymes is capable of catalysing lactose into an EPS.

In a preferred aspect the *Lactobacillus sake* spp., *Lactobacillus plantarum* spp. or *Lactobacillus salivarius* spp. produced enzymes is capable of catalysing lactose, raffinose, stacchyose or verbascose into an EPS.

In a preferred aspect the EPS produced by the *Lactobacillus sake* spp., *Lactobacillus plantarum* spp. or *Lactobacillus salivarius* spp. is a homo-EPS.

In a preferred aspect the homo-EPS produced by said *Lactobacillus sake* spp., *Lactobacillus plantarum* spp. or *Lactobacillus salivarius* spp. comprises at least a long chain polymer (polysaccharide) and/or a short chain polymer (oligosaccharide).

Preferably, the present invention provides a composition that can be used to ferment milk or any other equivalent thereof which is supplemented with yeast extract and magnesium ions for the production of a product for consumption containing structure forming EPS and/or nutritional oligosaccharides and/or polysaccharides.

Preferably, the present invention provides a composition that can be used to ferment milk or any other equivalent and produce yoghurt like ingredient containing structure forming EPS and/or nutritional oligosaccharides and/or polysaccharides.

Preferably, the present invention provides a composition which can be used as an ingredient to food wherein the live micro-organism, the EPS and/or the homo-EPS, the oligosaccharide and/or the polysaccharide component of the composition exhibit a beneficial effect on the gastrointestinal micro-flora of consumers.

In another preferred aspect, the present invention provides a composition which can be used as a food ingredient wherein the EPS and/or the homo-EPS and/or the oligosaccharides component and/or the polysaccharide component of the composition have immunomodulatory effect on the gastrointestinal immune system of consumers.

In another preferred aspect, the present invention provides a composition which can be used as a food ingredient wherein the EPS and/or the homo-EPS and/or the oligosaccharides and/or the polysaccharide components of the composition act as prebiotics when used as ingredients to products for consumption or to pharmaceutical products.

In another preferred aspect, the present invention provides a composition which can be used as a food ingredient wherein the EPS and/or the homo-EPS and/or the oligosaccharides and/or the polysaccharide components of the composition have the capacity to reduce the production of gas by the gastrointestinal micro-flora, when used as ingredients to products for consumption or to pharmaceutical products. That is the composition of the present invention can be used to reduce, limit or avoid the accumulation of gas in the gut and thereby lead to the reduction in flatulence.

Preferably the compositions for use in the present invention are in the form of concentrates which comprise a substantially high concentration of a viable micro-organism, and/or an enzyme produced by said microorganism and/or and EPS produced by said enzyme.

In another preferred aspect, the present invention provides a composition which is prepared in a medium which has an adjusted pH range such that the degree of conversion of sucrose and/or lactose to EPS can be modulated.

Advantages

Some advantages of the present invention are presented in the following commentary.

A primary advantage of the composition of the present invention is its capacity to improve the aroma, flavour, mildness, sweetness, consistency, texture, body, mouth feel, firmness, viscosity, gel fracture, wheying off, structure and/or organoleptic properties and nutrition of products for consumption containing said composition.

Another advantage is that the viable micro-organism of the composition of the present invention can produce enzymes that can produce EPS by utilizing as substrates different sugars such as sucrose, lactose, raffinose, stacchyose or verbascose.

Advantageously, since lactose can naturally be found in whey and milk, using the composition of the present invention it may be possible to modulate the whey concentration and viscosity of a product for consumption while balancing the sweetness of the product. In other words, depending on the intended application it would be possible, using the composition as described herein to generate products with tailored viscosity, water holding capacity and mouthfeel by adjusting the sweetness of the product for consumption. By reducing the lactose levels in the product, it may be possible to obtain a product that is suitable for consumption by lactose intolerant or by those who are allergic to lactose.

Advantageously, the composition of the present invention may be used to produce products for consumption based entirely on dairy products. In other words a product for consumption comprising the composition of the present invention can be produced from dairy products only, without addition of for example extra sucrose. By way of example dairy products produced without the addition of sucrose would be beneficial to the dental health of the consumers.

Another advantage of the composition of the present invention is the capacity of the lactic acid micro-organisms to convert lactose to a homopolysaccharide. The homopolysaccharide as described herein has a high water binding capacity and can also be used to modulate viscosity of the product for consumption.

For some applications, the composition of the present invention can lead to a significant decrease in syneresis (serum separation) and improve product stability.

It is recognised that consuming leguminous grains such as beans or soybeans can lead to the production of gas in the gastrointestinal tract that can lead to discomfort. Advantageously the present invention provides a composition which is capable of affecting such as decreasing, reducing or suppressing the production of gas by the gastrointestinal micro-organisms.

The composition of the present invention can also be used in combination with other components of products for consumption to deliver said improvements.

The present invention also covers using the composition of the present invention as a component of pharmaceutical combinations with other components to deliver medical or physiological benefit to the consumer.

It is also within the scope of the present invention to provide a composition comprising viable micro-organisms capable of producing an enzyme and an EPS where the expression and/or level of polymerisation have been modulated. The expression and/or level of polymerisation of the EPS in the composition can be modulated by varying the number of the viable micro-organism, by altering the fermentation temperature and/or the pH of the environment and/or by using an acceptor molecule such as maltose.

Accordingly, depending on the intended application, the present invention can also provide a composition which comprises viable micro-organism, an enzyme and EPS the expression and/or level of polymerisation of which has been modulated to suit the intended application.

Micro-Organism

Suitable viable micro-organisms for use in the present invention include bacteria, moulds and/or yeasts.

The term "viable micro-organism" means a micro-organism which is capable of normal growth and development. Also it is to be understood that where reference is made in the present specification, including the accompanying claims, to 'a' viable micro-organism or 'an' anti-microbial agent, such reference is meant to include one or more viable micro-organisms or one or more anti-microbial agents, and mixtures thereof, unless it is specifically stated otherwise in the text.

The micro-organism may be a naturally occurring micro-organism or it may be a transformed micro-organism. The micro-organism may also be a combination of suitable micro-organisms.

In a preferred aspect, the viable micro-organism of the present invention may be selected from a group comprising various strains of lactic acid bacteria such as *Lactococcus, Streptococcus, Pediococcus, Enterococcus, Leuconostoc, Carnobacterium, Propionibacterium, Bifidobacterium* and *Lactobacillus* genuses.

In a preferred aspect the viable micro-organism is *Leukonostoc mesenteriodes* spp.

In another preferred aspect the viable micro-organism is *Lactobacillus sake* spp, *Lactobacillus plantarum* spp. or *Lactobacillus salivarius* spp.

The present invention provides a viable lactic acid micro-organism which produces an effective and/or increased amounts of glycosyltransferase (transglycosylase) enzyme. The glycosyltransferase (transglycosylase) enzyme as described herein may be a glucosyl transferase or a fructosyl transferase.

Advantageously, where the product is a foodstuff, the viable micro-organism and/or enzyme produced by said micro-organism and/or EPS produced by said enzyme should remain effective through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

EPS

The EPS may be any suitable EPS that is obtainable from a lactic acid bacteria.

The EPS component of the composition may comprise homopolysaccharide molecules and/or heteropolysaccharide molecules.

As used herein the term "homopolysaccharide" or "homo-EPS" means a polysaccharide molecule which contains only one type of mono-saccharide molecule wherein the mono-saccharide molecule may be glucose or fructose.

As used herein the term "heteropolysaccharide" means a polysaccharide molecule which is constructed from two of more of mono-saccharide, di-, tri-, or tetra-saccharide units. By may of a non-limiting example, mono-saccharides include sugars such as glucose, fructose or galactose while di-saccharides include sugars such as maltose, lactose or sucrose.

The amount of EPS and thereby the viscosity of the medium can be modulated. The term "modulate" when used in the context of EPS and/or viscosity means that the level of polymerisation of the respective substrate can be regulated. In other words, it can be increased or decreased. Thus, the amount of EPS produced can be modulated for example by varying the number of viable micro-organisms, the length of the fermentation process, the temperature and the presence of different amount of maltose in the medium. Preferably the amount of EPS is modulated by varying the pH of the fermentation medium. The pH range at which the amount of EPS production may be increased is in the range from pH 5.5 to pH 6.9, preferably at pH from 5.7 to pH 6.7, more preferably at pH from 5.9 to pH 6.5. The pH at which the amount of EPS can be reduced, in the range from 4.0 to 5.4 or from 7.0 to 8.0.

Medium

The present invention also provides a medium comprising a viable lactic acid micro-organism, which produces effective and/or increased amounts of an enzyme capable of catalysing an EPS for improving the aroma, flavour, mildness, sweetness, consistency, texture, body, mouth feel, firmness, viscosity, gel fracture, wheying off, structure and/or organoleptic properties, nutrition and/or health benefits to product for consumption.

The present invention provides a medium comprising a viable lactic acid micro-organism which comprises effective and/or increased amounts of glycosyltransferase (transglycosylase) enzyme or a fructosyl transferase enzyme.

In addition, the present invention provides a medium comprising a viable lactic acid micro-organism which produces effective and/or increased amounts of a glycosyl transferase (transglycosylase) enzyme or fructosyl transferase enzyme capable of polymerising sucrose and converting it into an EPS which comprises at least a long chain polysaccharide or a short chain oligosaccharide which may be used as a food component with optimised nutritional and health benefit.

Also the present invention provides a medium comprising a viable lactic acid microorganism which produces effective and/or increased amounts of a glycosyl transferase (transglycosylase) enzyme or fructosyl transferase enzyme which is capable of polymerising lactose and converting it into an EPS. The formed EPS comprises at least a long chain polysaccharide or a short chain oligosaccharide which may be used as a food component with optimised nutritional and health benefit. The EPS which is formed using lactose as an enzyme substrate may also be used in medical applications such as blood substitute.

Also the present invention provides a medium comprising a viable lactic acid microorganism which produces effective and/or increased amounts of a glycosyl transferase (transglycosylase) or fructosyl transferase capable of polymerising maltose and converting it into an EPS which comprises at least a long chain polysaccharide or a short chain oligosaccharide which may be used as a food component with optimised nutritional and health benefit.

Also the present invention provides a medium comprising viable *Leuconostoc mesenteroides* which produces effective and/or increased amounts of a glycosyl transferase (transglycosylase) or fructosyl transferase capable of polymerising raffinose, stacchyose or verbascose into EPS which comprises at least a long chain polysaccharide or a short chain oligosaccharide which may be used as a food component with optimised nutritional and health benefit. The formed EPS comprises at least a long chain polysaccharide or a short chain oligosaccharide which may be used as a food component with optimised nutritional and health benefit. The composition comprising the viable *Leuconostoc mesenteroides* which produces effective and/or increased amounts of a glycosyl (transglycosylase) or fructosyl transferase capable of polymerising raffinose, stacchyose or verbascose into EPS may also be used as an ingredient in products for consumption which are characterised with a reduced gas production and/or a reduced flatulence.

In addition, the present invention provides a medium comprising viable *Lactobacillus sake* spp., *Lactobacillus plantarum* spp. or *Lactobacillus salivarius* spp. which can produce effective and/or increased amounts of the enzyme glucan sucrase which is capable of polymerising sucrose and converting it into EPS. The formed EPS comprises at least a long chain polysaccharide or a short chain oligosaccharide and may be used as a food component with optimised nutritional and health benefit. The EPS which is formed by *Lactobacillus sake* spp., *Lactobacillus plantarum* spp. or *Lactobacillus salivarius* spp. using sucrose as a substrate is a homo-exopolysaccharide comprising glucose molecule monomers.

Also the present invention provides a medium comprising viable *Lactobacillus sake* spp., *Lactobacillus plantarum* spp. or *Lactobacillus salivarius* spp. which produce effective and/or increased amounts of the enzyme glucan sucrase which is capable of polymerising lactose and converting it into an EPS. The formed EPS comprises at least a long chain polysaccharide or a short chain oligosaccharide which may be used as a food component with optimised nutritional and health benefit. The EPS which is formed using lactose as a substrate may also be used in medical application such as blood substitute.

Also the present invention provides a medium comprising viable *Lactobacillus sake* spp., *Lactobacillus plantarum* spp. or *Lactobacillus salivarius* spp. which produce effective and/or increased amounts of the enzyme glucan sucrase which is capable of polymerising raffinose, stacchyose or verbascose and polymerising them to EPS. The formed EPS comprises at least a long chain polysaccharide or a short chain oligosaccharide which may be used as a food component with optimised nutritional and health benefit. The composition comprising the viable *Lactobacillus sake* spp., *Lactobacillus plantarum* spp. or *Lactobacillus salivarius* spp. which produce effective and/or increased amounts of the enzyme glucan sucrase and the EPS which is formed from raffinose, stacchyose or verbascose as a substrate may be used as an ingredient in products for consumption which are characterised with a reduced gas production or a reduced flatulence. A product for consumption which contains an EPS formed from raffinose, stacchyose or verbascose may be used to increase the beneficial, health promoting bacteria in the gastrointestinal tract. In other words, the composition of the present invention has a potential of playing a prebiotic role in the gastrointestinal tract. Also, it is known that bloating can be due to an array of factors such as abnormal fermentation or irregular fermentation pattern which can be alleviated by among others the prebiotic effect of the composition of the present invention.

While preparing the composition of the present invention, it is also possible to adjust the ratio of sucrose/maltose, lactose/maltose or stacchyose/maltose of the medium during the fermentation such that a targeted molecular weight distribution of polysaccharide or oligosaccharide can be obtained. The ability to control the molecular weight of the polysaccharide or oligosaccharide can be used for regulating the viscosity of the products comprising the composition of the present invention.

As used herein, the term "polysaccharide" refers to a carbohydrate molecule which is composed of more than 10 sugar units where one sugar unit can be a mono-saccharide, di-, tri-, or tetra-saccharides.

Also used herein the term "oligosaccharide" refers to a carbohydrate molecule which comprises less than 10 sugar molecules where the sugar molecules can be any one or more of mono-saccharides, di-, tri-, and tetra-saccharides.

Preferably, the polysaccharide and/or the oligosaccharide is composed of mono-saccharides and/or di-saccharides. By way of example, mono-saccharides include but are not limited to sugars such as glucose and fructose and di-saccharides include but are not limited to sugars such as sucrose, lactose and maltose.

Thus, in one aspect of the present invention, the medium may optionally be supplemented with any one of a mono-saccharide, di-, tri-, or tetra-saccharide. Here, the composition that is produced by the viable lactic acid micro-organism has one or more EPS wherein at least some (preferably a large proportion) of the EPS is/are homopolysaccharide molecules.

In another aspect, the medium which may be used in the process of the present invention may optionally be supplemented with two or more of mono-saccharide, di-, tri-, or tetra-saccharides. Here, the composition that is produced by the viable lactic acid micro-organism has one or more EPS wherein at least some (preferably a large proportion) of the EPS is/are heteropolysaccharide molecules.

In another aspect, the medium which may be used in the process of the present invention may optionally be supplemented with yeast extract and magnesium ions ($Mg^{2+}$) in order to assist growth of the lactic acid micro-organisms.

In a preferred aspect, the medium is an edible medium. The term "edible medium" means any growth medium which can support *lactobacilli* growth and which is commercially acceptable for consumption such as for instance milk from animal, plant or synthetic origin or lactic medium as described in the Examples. Also, depending on the intended use, the composition provides for use of an edible medium which is not supplemented with any extra mono-saccharide, di-, tri-, or tetra-saccharide. Thus, in one embodiment, the viable lactic acid micro-organism component of the composition of the present invention produces an enzyme which is capable of polymerising lactose which is naturally found in dairy products such as milk or whey. The capacity of the viable lactic acid micro-organism component of the composition of the present invention to produce an enzyme which polymerises lactose would allow for the production of products for consumption which have low, significantly reduced or are essentially lactose free. Such products for consumption would be suitable for consumption by lactose intolerant or lactose allergic consumers. The capacity of the viable lactic acid micro-organisms to polymerise lactose would allow for the production of dairy products without sucrose. Such sucrose free products would have a reduced detrimental effect on the teeth.

While preparing the composition of the present invention, it is also possible to adjust the pH of the medium during the fermentation such that a targeted amount of EPS can be obtained. The ability to control the amount of EPS can be used for regulating the viscosity of the products comprising the composition of the present invention.

Thus, in one aspect of the present invention, the pH of the medium can be adjusted such that the degree of conversion of sucrose or lactose to EPS can be controlled. Here, the pH of the composition may be adjusted such that an amount of EPS is produced which can lead to a modulation in the viscosity of the medium. In addition, different pH conditions may lead to change in the viscosity of the composition by increasing or decreasing the levels of branching of the EPS structure.

Preparation of the Composition

The composition may be prepared by an in situ process—of the type mentioned herein. In this case, suitable micro-organisms or active glycosyltransferase (transglycosylase) enzyme is present in an edible medium that can support the conversion of sucrose or lactose or other substrates into EPS. The in situ produced composition can then be processed in order to provide a composition which is suitable for different applications. By way of example, the composition can be freeze dried, spray dried or any other way of cryopreservation. It is intended that the different ways of processing the composition maintain the viability of the lactic acid micro-organisms. It is envisaged that the presence of EPS may increase the survival rate of the lactic acid micro-organisms of the composition. Thus the EPS may be capable of protecting the lactic acid micro-organisms during cryopreservation.

Optionally, the components of the composition can be prepared in isolation and then the components may be combined together to form the composition. By way of example EPS can be produced in situ by growing lactic acid bacteria in a commercially acceptable medium under conditions where EPS is formed. The resulting EPS can be isolated from the fermentation media by any suitable technique e.g. by means of a precipitation using an organic solvent in which the EPS is not soluble or has limited solubility. Another way of isolating the EPS is by removal of the water, e.g. by evaporation, membrane filtration or spray drying. By producing the EPS in a commercially acceptable medium, a product for consumption containing said EPS will not require labelling as containing an additive. By commercially acceptable medium it is meant any medium capable of being used as a medium to produce the composition of the present invention.

In one embodiment of the present invention, the commercially acceptable medium is supplemented with yeast extract and magnesium ions. The yeast extract added to the medium can be in the range between 0.01% and 1% of the total volume of the medium. Preferably the yeast extract added to the commercially acceptable medium is in the range between 0.025% to 0.9%, more preferably between 0.1% to 0.5%, even more preferably between 0.25% to 0.7%.

Alternatively, the composition of the present invention can be synthesised for example by recombinant micro-organisms, which do not necessarily have to be lactic acid micro-organisms.

The term "recombinant micro-organism" means a micro-organism which carries a recombinant nucleotide sequence coding for an enzyme which is capable of producing EPS such that both the enzyme and the EPS can be used as components of the composition of the present invention.

Furthermore, the lactic acid micro-organism component of the composition of the present invention may also be grown separately in a commercially acceptable medium to a cell density such that it does not form EPS or enzyme which produces said EPS. It is important that the viability of the resulting culture is maintained which can be achieved by different methods known in the art for example by spray drying or freeze drying.

The process of the present invention can be used for in situ production of the composition comprising growing said lactic acid bacteria in a commercially acceptable medium such as dairy liquid medium optionally supplemented with extra carbon source which is also a suitable enzyme substrate such as the disaccharides sucrose and/or maltose under conditions where enzyme is produced and EPS is formed. The ratios of the disaccharides can be varied or adjusted during fermentation so that a targeted molecular weight distribution of polymer can be achieved. Therefore, by altering the sucrose and/or maltose ratios it is possible to artificially regulate the polymerisation process and thus modulate viscosity. Preferably the product obtained by said process is not thereafter subjected to an intensive shear treatment. Such culture containing said composition or optionally each isolated component can advantageously be added into dairy ingredient-containing products such as dressings, margarine, mayonnaise, and spreads, and low-fat or zero-fat substitutes thereof, yoghurt based drinks and others.

Thus, it is also within the scope of the present invention that by altering the ratios of maltose to sucrose or maltose to lactose it is possible to modulate the degree of EPS polymerisation using maltose as an acceptor molecule.

Large Scale Application.

In one preferred embodiment of the present invention, the composition is used for large scale applications.

Preferably the composition is produced in a quantity of from 0.1% per liter to about 10% per liter of the total cell culture volume after cultivation of the lactic acid microorganism.

Preferably the composition is produced in a quantity of from 0.5% per liter to about 7.5% per liter of the total cell culture volume after cultivation of the lactic acid microorganism.

Preferably the amino acid sequence is produced in a quantity of from 2.5% per liter to about 5% per liter of the total cell culture volume after cultivation of the lactic acid microorganism.

Composition

The composition of the present invention can lead to improved aroma, flavour, sweetness, mildness, consistency, texture, body, mouth feel, firmness, viscosity, gel fracture, structure and/or organoleptic properties and nutrition of products for consumption containing said composition. Furthermore, the composition of the present invention can also be used in combination with other components of products for consumption to deliver said improvements.

Although it is preferred that the composition of the present invention is used to improve the aroma, flavour, mildness, sweetness, consistency, texture, body, mouth feel, firmness, viscosity, gel fracture, structure, smoothness of the surface and/or organoleptic properties and nutrition of products for consumption containing said composition—the present invention also covers using the composition of the present invention as a component of pharmaceutical combinations with other components to deliver medical or physiological benefit to the consumer.

Combination with Other Components

The composition of the present invention may be used in combination with other components. Thus, the present invention also relates to combinations.

The combination of the present invention comprises the composition of the present invention and another component which is suitable for animal or human consumption and is capable of providing a medical or physiological benefit to the consumer.

Other components of the combinations of the present invention include polydextrose, such as Litesse®, and/or a maltodextrin. These other components may be optionally added to the composition to assist the drying process and help the survival of the micro-organisms.

Further examples of other suitable components include one or more of: thickeners, gelling agents, emulsifiers, binders, crystal modifiers, sweetners (including artificial sweeteners), vitamins, minerals, rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilizing them.

The term "stabiliser" as used here is defined as an ingredient or combination of ingredients that keeps a product (e.g. a food product) from changing over time.

The term "emulsifier" as used herein refers an ingredient (e.g. a food product ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers. Aeration can occur in a three phase system where air is entrapped by liquid oil then stabilised by agglomerated fat crystals stabilised with an emulsifier. Emulsifiers have a polar group with an affinity for water (hydrophilic) and a non-polar group which is attracted to oil (lipophilic). They are absorbed at the interfaces of the two substances, providing an interfacial film acting to stabilise the emulsion. The hydrophilic/lipophilic properties of emulsifiers are affected by the structure of the molecule. These properties are identified by the hydrophilic/lipophilic balance (HLB) value. Low HLB values indicate greater lipophilic tendencies which are used to stabilise water-in-oil emulsions. High HLB values are assigned to hydrophilic emulsifiers, typically used in oil-in-water emulsions. These values are derived from simple systems. Because foods often contain other ingredients that affect the emulsification properties, the HLB values may not always be a reliable guide for emulsifier selection.

As used herein the term "binder" refers to an ingredient (e.g. a food ingredient) that binds the product together through a physical or chemical reaction. During "elation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

The term "crystal modifier" as used herein refers to an ingredient (e.g. a food ingredient) that affects the crystallisation of either fat or water. Stabilisation of ice crystals is important for two reasons. The first is directly related to the product stability from a separation standpoint. The more freeze/thaw cycles a product encounters, the larger the ice crystals become. These large crystals can break down product structure, either naturally occurring, as in the case of cell walls, or that which is created by "elation". Because the water is no longer held in place, the product may exhibit syneresis, or weeping, after thawing. Secondly, in the case of a product which is consumed frozen, these large crystals result in an undesirable, gritty mouth feel.

"Carriers" or "vehicles" mean materials suitable for compound administration and include any such material known in the art such as, for example, any liquid, gel, solvent, liquid diluent, solubilizer, or the like, which is non-toxic and which does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the composition of the present invention when admixed with any other components, the lactic acid micro-organisms remain viable.

As used herein the term "component suitable for animal or human consumption" means a compound which is or can be added to the composition of the present invention as a supplement which may be of nutritional benefit, a fibre substitute or have a generally beneficial effect to the consumer. The ingredients can be used in a wide variety of products that require gelling, texturising, stabilising, suspending, film-forming and structuring, retention of juiciness, without adding unnecessary viscosity. Preferably, the ingredients will be able to improve the shelf live and stability of the viable culture.

The components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

The optimum amount of the composition to be used in the combination of the present invention will depend on the product to be treated and/or the method of contacting the product with the composition and/or the intended use for the same. The amount of viable micro-organism and/or enzyme produced by said micro-organism and/or EPS produced by said enzyme used in the compositions should be a sufficient amount to be effective and to remain sufficiently effective in improving the aroma, flavour, mildness, consistency, texture, body, mouth feel, viscosity, structure and/or organoleptic properties, nutrition and/or health benefits of food products containing said composition. This length of time for effectiveness should extend up to at least the time of utilisation of the product.

Concentrates

The compositions for use in the present invention may be in the form of concentrates. Typically these concentrates comprise a substantially high concentration of a viable micro-organism, and/or an enzyme produced by said microorganism and/or and EPS produced by said enzyme.

Powders, granules and liquid compositions in the form of concentrates may be diluted with water or resuspended in water or other suitable diluents, for example, an appropriate growth medium such as milk or mineral or vegetable oils, to give compositions ready for use.

The combinations of the present invention in the form of concentrates may be prepared according to methods known in the art.

In one aspect of the present invention the product is contacted by a composition in a concentrated form. Preferably, the product is contacted by a spray-dried and/or resuspended composition.

The compositions of the present invention may be spray-dried or freeze-dried by methods known in the art.

Typical processes for making particles using a spray drying process involve a solid material which is dissolved in an appropriate solvent (e.g. a culture of a micro-organism in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Products

Any product which can benefit from the composition may be used in the present invention. These include but are not limited to fruit conserves and dairy foods and dairy food-derived products, cosmetic and pharmaceutical products.

By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, filing for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat & lite natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

For certain aspects, preferably the present invention may be used in connection with yoghurt production, such as fermented yoghurt drink, yoghurt, drinking yoghurt, cheese, fermented cream, milk based deserts and others.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the aroma, flavour, mildness, sweetness, consistency, texture, body, mouth feel, firmness, viscosity, gel fracture, wheying off, structure and/or organoleptic properties, nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: improving the aroma, flavour, mildness, consistency, texture, body, mouth feel, viscosity, structure, serenity and/or organoleptic properties, nutrition and/or health benefits.

The compositions of the present invention may be applied to intersperse, coat and/or impregnate a product with a controlled amount of a viable micro-organism and/or enzyme produced by said micro-organism and/or EPS produced by said enzyme. Mixtures of viable micro-organisms and enzyme produced by said micro-organism and EPS produced by said enzyme may also be used and may be applied separately, simultaneously or sequentially.

Food

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

Preferably, the composition is used to ferment milk or sucrose fortified milk or lactic media with sucrose and/or maltose where the resulting media containing all components of the composition—i.e. said *lactobacilli*, and/or said enzyme and/or said EPS—can be added as an ingredient to yoghurt milk in suitable concentrations—such as for example in concentrations of from about 0.1% to about 10% before or alternatively after the fermentation of the yoghurt. The addition of the composition leads to an increase in viscosity and provides a firm mouth feel yoghurt, reduction in serenity (serum separation) and with an improvement in organoleptic properties of the end product.

Food Ingredient

The composition of the present invention may be used as a food ingredient.

As used herein the term "food ingredient" includes a formulation which is or can be added to functional foods or foodstuffs as a nutritional supplement and/or fiber supplement. The term food ingredient as used here also refers to formulations which can be used at low levels in a wide variety of products that require gelling, texturising, stabilizing, suspending, film-forming and structuring, retention of juiciness and improved mouthfeel, without adding viscosity.

The food ingredient may be in the from of a solution or as a solid—depending on the use and/or the mode of application and/or the mode of administration.

Food Supplements

The composition of the present invention may be—or may be added to—food supplements.

Functional Foods

The composition of the present invention may be—or may be added to—functional foods.

As used herein, the term "functional food" means food which is capable of providing not only a nutritional effect and/or a taste satisfaction, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

Fibre Supplement

In another aspect, the composition of the present invention may be used as—or in the preparation of—a fibre supplement.

Initially, the success of a food product virtually hinged on the word "fibre" or, subsequently, "bran". Despite conflicting studies on fibre's specific health attributes, the overall consensus among experts and consumers is that most people need more fibre in their diet. Fibre has further proven to be useful for its functional properties, such as water absorption and bulk-building in reduced-fat foods.

Fibre has gone by a number of names over the years, including "roughage," "bulk", "bran", "fibre", "plant residue", "plantix" and "unavailable carbohydrates". Even today, devising a concise, yet complete, definition for dietary fibre is no simple task because dietary fibre is a complex matrix of various components defined differently among various scientific disciplines.

Here, the term fibre is used in the context of food and as such it is referred to as non-digestible material. Specifically, fibre consists of cellulose, hemicellulose, pectins, gums, mucilages and lignin.

Not every fibre source contains all of these components. Actually, it is the sheer number of potential combinations that results in the wide variety of different physiological and functional effects observed in different fibre ingredients. By the same token, not every fibre source is 100% dietary fibre.

"Total dietary fibre (TDF) is defined as non-digestible carbohydrates," says Diane Lardiere, national sales and marketing manager, Canadian Harvest, Cambridge, Minn. "Wheat bran is only 40% TDF, but is considered a fiber ingredient".

Thus, the composition of the present invention may be added to—fiber supplements.

It is within the scope of the present invention that the composition is used as a supplement to a diet in combination with different conventional fiber sources as detailed above. The recommended dose of fiber intake for adults is between 20 and 35 grams per day or 10-13 grams per every 1000 calories consumed and for children, generally, the intake is based on their age or weight 0.5 grams of fiber per kilogram of body weight (or 0.23 grams per pound of body weight) with an upper limit of 35 grams of fiber per day.

It is also within the scope of the invention to provide a means ensuring that the recommended daily fiber intake (20-35 grams per day or 10-13 grams per every 1000 calories consumed) is achievable. Such tablets, pills, capsules, ovules, solutions or suspensions, can be formulated to substitute for meals and snacks, especially during the beginning of a weight-loss program.

Importantly from a health point of view, when fiber tablets, pills, capsules, ovules, solutions or suspensions are taken with meals, it helps reduce the consequent rise in blood glucose after eating and enhances satiety.

It is also within the scope of this application that the composition of the present invention be incorporated in a fiber beverage. Research has indicated that soluble fiber, may help support digestive health and that a diet high in soluble fiber (at least 25 grams per day) may help maintain normal cholesterol levels.

Probiotic

For some applications, it is believed that the viable lactic acid micro-organisms in the composition of the present invention can exert a probiotic culture effect. Here, a prebiotic is:

"a non-digestible food ingredient that beneficially affects the host by selectively stimulating the growth and/or the activity of one or a limited number of bacteria in the colon." (*Am Clin Nutrit*, 2001; 73:406S-409S.).

According to the latest consensus report (van Loo et al., 1999, *Br. J. Nutr.*, 81: 121-132) the definition for prebiotic is an increase in the number and/or activity of mainly bifidobacteria or lactic acid bacteria in the gastrointestinal tract. Here, it is known that: bifidobacteria may help fight a wide range of harmful and food-poisoning bacteria, including the potentially fatal *E. coli* 0157 and *E. coli* H88; bifidobacteria can prevent young children suffering from diarrhoea; *Lactobacillus* GG can be helpful in treating antibiotic-associated diarrhoea; and *Lactobacillus* GG has also been shown effective at treating some cases of travellers' diarrhoea and rotavirus infection, the most common cause of diarrhoea in children world wide.

It is also within the scope of the present invention to add to the composition of the present invention further probiotic cultures.

The term "probiotic culture" as used herein defines live micro-organisms which beneficially affect the host organism by improving its intestinal microbial balance. The term "probiotic" as used herein also encompasses live micro-organisms that can stimulate the beneficial branches of the immune system and at the same time decrease the inflammatory reactions in the gut. In this regard, the use of the composition of the present invention, containing said probiotic ingredient for anti-cancer therapy and prevention of allergies and ulcerative colitis is also contemplated.

Whilst there are no lower or upper limits for probiotic intake, it has been suggested that at least 10,000 viable cells per ml of product will give the micro-organism a competitive chance within the gut flora.

In addition to the prebiotic effect of the composition of the present invention, it is also within the scope of the present invention to provide prebiotics as other compounds which can be included in a combination along with the composition. The prebiotic component of the combination comprising the composition of the present invention are characterised with slow fermentation in the large bowel. Such prebiotics can exert a positive effect on the gut flora, specifically in the left side of the colon, an area of the gut which is especially prone to disorders in particular bowel cancer and ulcerative colitis.

Synbiotic

The present invention also contemplates using both pre- and probiotics as ingredients in a combination along with the composition of the present invention which when combined, become synbiotics. The purpose of this is to combine the effects of new beneficial bacteria and the stimulation of the body-own beneficial bacteria. There is a high potential in the development and the consumption of such mixtures, since some of these may well show powerful synergistic nutritional effects.

Thus the composition of the present invention may be specifically designed to contain different components which can provide a symbiotics effect to the consumer.

Pharmaceutical

The composition of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the from of a solution or as a solid—depending on the use and/or the mode of application and/or the mode of administration.

Pharmaceutical Ingredient

The composition of the present invention may be used as pharmaceutical ingredients. Here, the composition may be the sole active component or it may be at least one of a number (i.e. 2 or more) active components.

The pharmaceutical ingredient may be in the from of a solution or as a solid—depending on the use and/or the mode of application and/or the mode of administration.

Forms

The composition of the present invention may be used in any suitable form—whether when alone or when present in a combination with other components or ingredients. Likewise, combinations comprising the composition of the present invention and other components and/or ingredients (i.e.

ingredients—such as food ingredients, functional food ingredients or pharmaceutical ingredients) may be used in any suitable form.

The composition the present invention may be used in the form of solid or liquid preparations or alternatives thereof. Examples of solid preparations include, but are not limited to tablets, capsules, dusts, granules and powders which may be wettable, spray-dried, freeze-dried or lyophilised. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fiber capsules, fiber tablets etc. or even fiber beverages.

EXAMPLES

The present invention will now be described by way of examples, and with reference to the accompanying figures:

FIGURES

Figure 1:
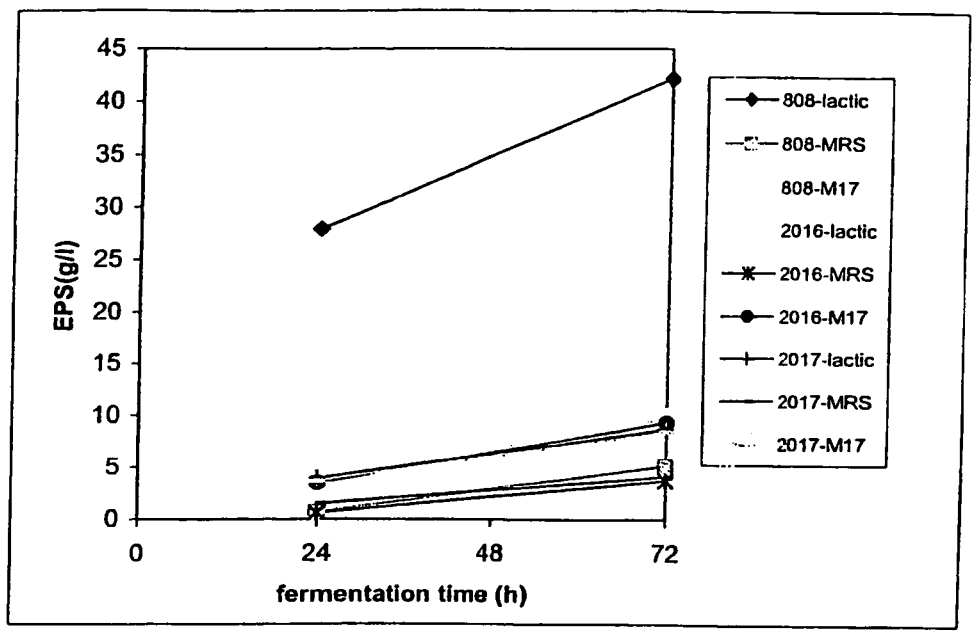

FIG. 1. Evaluation of best strain for exopolysaccharide (EPS) production.

FIG. 2. Evaluation of cell count of EPS producing strains.

Figure 3:
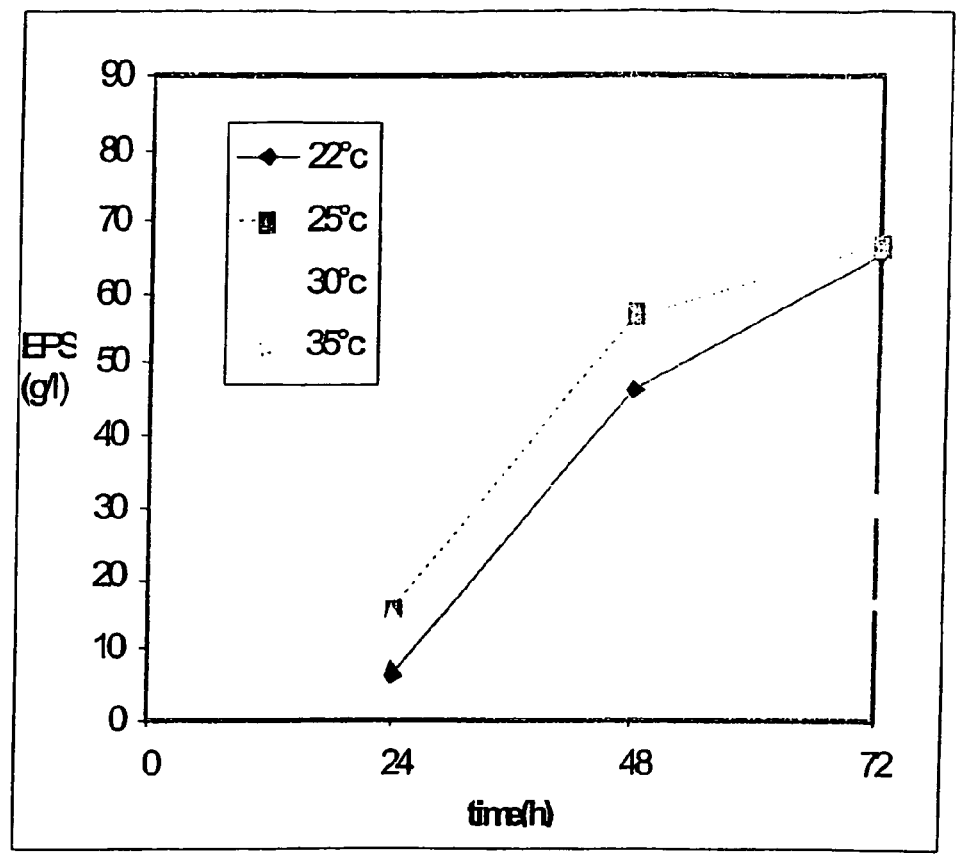

FIG. 3. Evaluation of best temperature for EPS production using *Leuconostoc mesenteroides* 808 strain.

Figure 4:
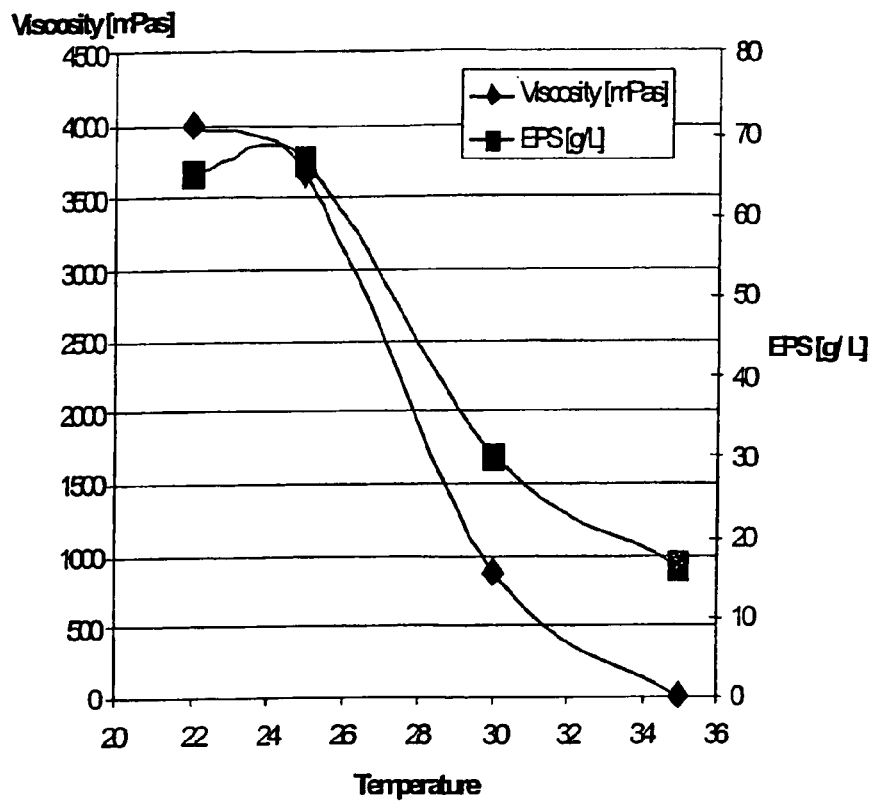

FIG. 4. Evaluation of EPS production and viscosity increase using *Leuconostoc mesenteroides* 808 strain.

Figure 5A:
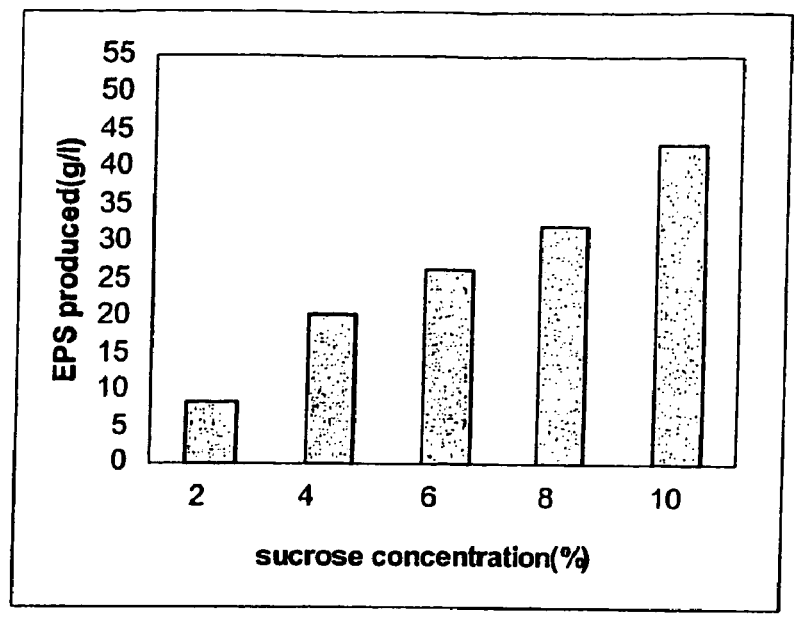

FIG. 5A. Evaluation of EPS production at different sucrose concentrations using *Leuconostoc mesenteroides* 808 strain.

Figure 5B:
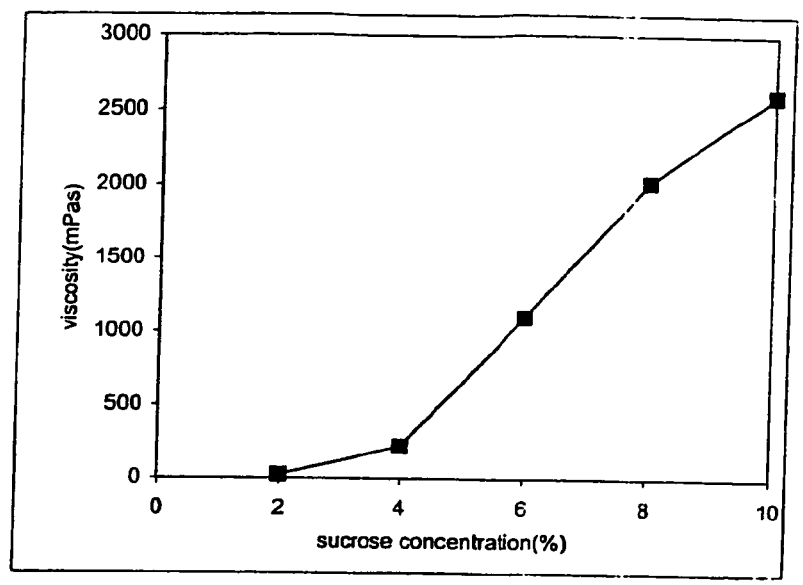

FIG. 5B. Evaluation of viscosity increase at different sucrose concentrations using *Leuconostoc mesenteroides* 808 strain.

Figure 6:
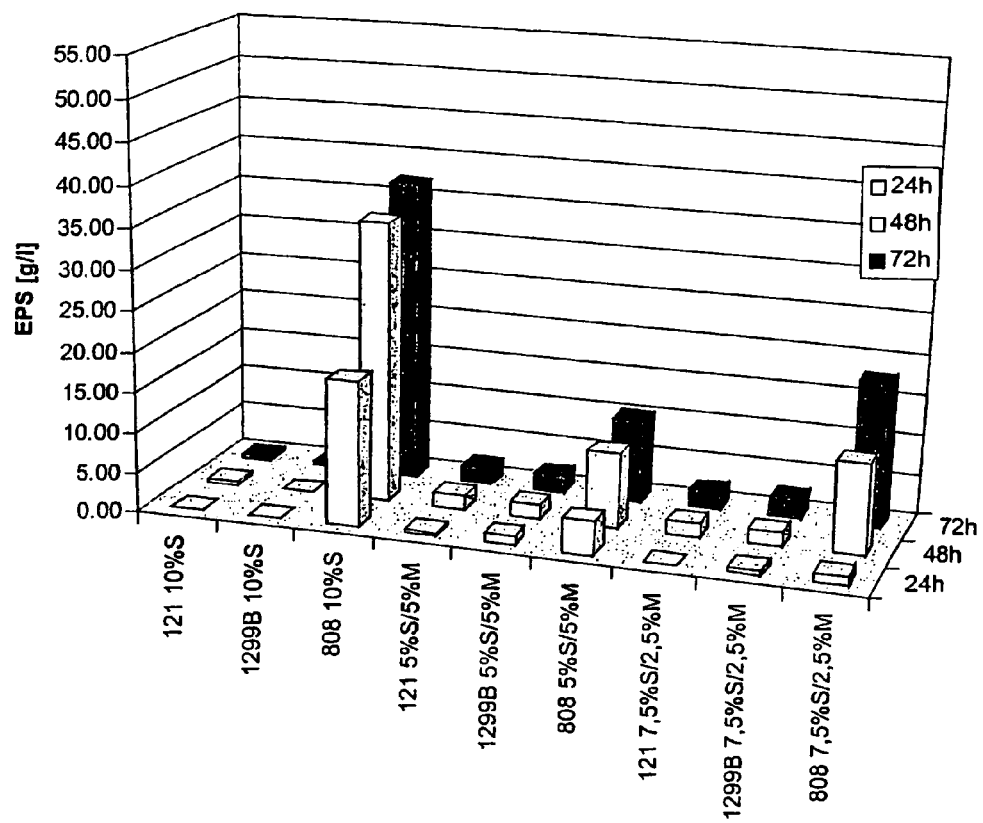

FIG. 6. EPS production by *Leuconostoc mesenteroides* strains in medium containing different amounts of maltose.

Figure 7:
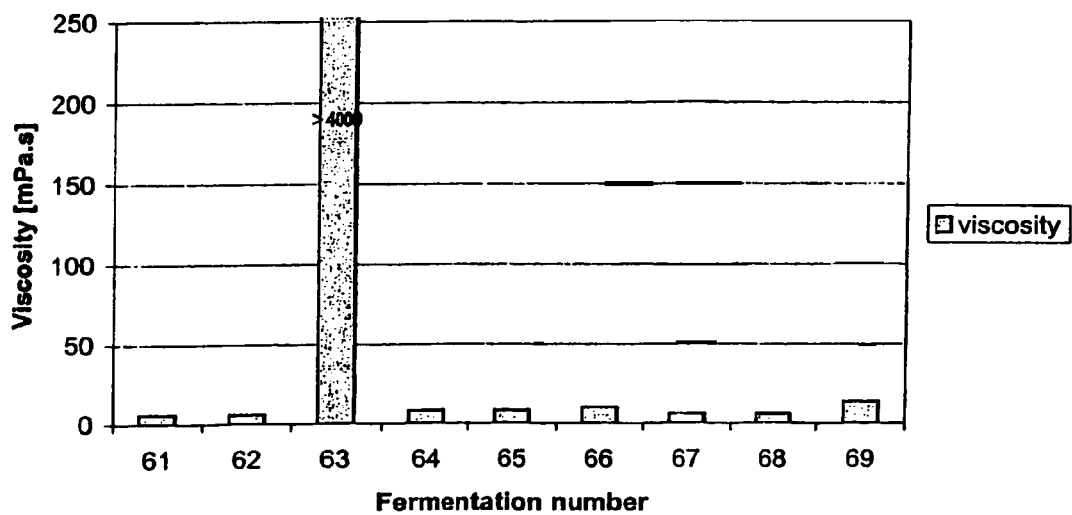

FIG. 7. Changes in viscosity produced by *Leuconostoc mesenteroides* 808 strain in a growth medium containing different amounts of maltose.

FIG. 8. EPS production by *Lactobacillus sakei* 570 strain in sucrose/maltose and lactose supplemented growth medium.

FIG. 9. EPS production by *Lactobacillus plantarum* 853 strain in sucrose/maltose and lactose supplemented growth medium.

FIG. 10. EPS production by *Lactobacillus salivarius* 1502 strain in sucrose/maltose and lactose supplemented growth medium.

FIG. 11. Effect of maltose on the EPS produced by *Leuconostoc mesenteroides* 808, *Lactobacillus sakei* 570, *Lactobacillus plantarum* 853 and *Lactobacillus salivarius* 1502; production of oligosaccharides and EPS production from lactose as an enzyme substrate.

FIG. 12. EPS production by *Leuconostoc mesenteroides* 808 in sucrose supplemented growth medium at different pH conditions.

FIG. 13. EPS production by *Lactobacillus sakei* 570 in sucrose supplemented growth medium at different pH conditions.

FIG. 14. EPS production by *Lactobacillus plantarum* 853 in sucrose supplemented growth medium at different pH conditions FIG. 15. Viscosity of *Leuconostoc mesenteroides* 808 in sucrose supplemented growth medium at different pH conditions.

FIG. 16. Viscosity of *Lactobacillus sakei* 570 in sucrose supplemented growth medium at different pH conditions.

FIG. 17. Viscosity of *Lactobacillus plantarum* 853 in sucrose supplemented growth medium at different pH conditions.

FIG. 18. EPS structure analysed by NMR.

FIG. 19. Spray drying of *Leuconostoc mesenteroides* 808 strain containing EPS.

METHODS

Screening

In order to establish which lactic acid bacterial strains are capable of producing EPS for the purposes of the present invention, a number of different strains were screened. Samples of *Leuconostoc mesenteroides* 808, *Lactobacillus plantarum* 853 and *Lactobacillus salivarius* 1502 have been deposited at the Deutsche Sammlung von Mikroorganismen und Zellkulturen GmbH. The accession numbers are DSM 15792 ["DC 808"], DSM 15793 ["DC 853"] and DSM 15794 ["DC 1502"] respectively. The depositor [Danisco Niebull GmbH, Busch-Johannsen Str. 1, 25899 Niebull] have authorised the applicant to refer to the deposited biological material in the application and given unreserved and irrevocable consent to the deposited material being made available to the public. Samples of *Lactobacillus sakei* 570 was deposited at the Deutsche Sammlung von Mikroorganismen und Zellkulturen GmbH, currently located at Inhoffenstraße 7 B, 38124 Braunschweig, Germany, under the terms of the Budapest Treaty on Sep. 2, 2003. The accession number for *Lactobacillus sakei* 570 is DSM 15889.

The screening method involved the following steps:

Micro-organisms of each strain were activated/inoculated in 10 ml Lactic media or 9% skim milk-media (containing 0-2% sucrose) and incubated at 25-42° C. for 8-20 h to form a pre-culture.

The pre-culture was subsequently transferred into micro-titre plates. Each well from the micro-titre plates contained 0.2-2 ml Lactic media or 9% Skim milk-media. Each well, which already contained the chosen growth medium, was then inoculated with 1-5% pre-culture and incubated at 25-42° C. for 8-20 h.

Culture from each cavity was then transferred to the surface of a solid lactic media with the aid of a 96-replicator and incubated at 25-42° C. for a further 8-20 h.

After this incubation period, colonies were examined by eye or in some cases with the aid of a light microscope at magnification setting 10× to identify colonies which exhibit a slimy bubble (EPS). Colonies which contained a slimy bubble were identified as positive and subjected to further analysis.

Fermentation:

An activation overnight culture is prepared in Lactic or a milk-based media (as set forth above). 1% of this overnight culture is transferred into a media containing at least 2% sucrose and is incubated under fermentation conditions (25-42° C., 8-20 h, pH 5.8-7). The fermentation chamber is then inoculated with 1-5% of these pre-cultures.

Lactic growth media (lactic 100b) typically contains: 2% pepton (Merck, Germany), 0.5% yeast extract, 0.25% gelatine, 0.4% NaCl, 0.25% Sodium acetate, 0.05% L-ascorbic acid, 0.05% Tween 80, at least 2% sucrose.

EPS-Measurement

After separation from contaminants such as proteins the amount of EPS is measure gravimetrically by precipitation with a double volume of chilled (4° C.) 96% Ethanol. The precipitate can optionally be incubated at 4° C. for several hours to improve the precipitation step after which the precipitated EPS is sedimented by centrifugation and air dried or preferably freeze dried.

In More Detail:

3 ml of the culture from the fermentation chamber culture is added to 6 ml 4° C. cold 96% Ethanol.

The resulting mixture is then mixed with the aid of a vortex and is then stored overnight at 4° C.

After the overnight incubation at 4° C., the precipitate is centrifuged for 15 min at 2500 rpm.

The supernatant is aspirated and the pellet dried for 4-6 h at 80° C.

Viscosity Measurements.

The viscosity of the lactic growth medium supplemented with varying amounts of maltose following fermentation was measured using the DV II Viscometer (UT 401) following the Manufacturer's instructions.

Purification of Hexaglucan from Lb 570

The heat-treated ferment was centrifuged at 10,000 rpm for 10 min in order to remove the cells. The EPS in the supernatant was then precipitated with 2× volume 96% ethanol and centrifuged at 12,500 rpm for 15 min. The EPS was dried at 60° C. over night. The EPS was redissolved in water at a concentration of 5 mg/ml.

Partial hydrolysis of EPS was performed in 50 mM TFA at 100° C. for 6 hrs. The sample was dried and dissolved in water at a concentration of 35 mg/ml. The non-hydrolysed EPS was precipitated with isopropanol (1:1 v/v). After centrifugation at 10 000 rpm for 10 min the supernatant was dried down to half of the volume. The sample is filtered trough 0.45 μm filter and separated on the DIONEX™ PA1 column. A sample volume of 23 μl was loaded on the column and eluted with buffer A (0.1 M NaOH) and buffer B (1 M Na-acetat in 0.1 M-NaOH) with the following gradient: 0-25 min: isocratic with 5% B, 25-34 min: 5-8% B, 34-34.001 min: 8-100% B, 34.001-44: isocratic 100% B, 44-44.001; 100-5% B, 44.001-54: isocratic 5% B. During the run the peaks were automatically desalted by a DIONEX™ desalting device CMD™ and collected. The hexaglucan was analysed by NMR.

The heptaglucan from Ln 808 was purified with the same procedure except that the partial hydrolysis was performed in 500 mM TFA. The peak containing the heptaglucan was re-run on PA1 column under the same conditions in order to be more purified.

NMR Spectroscopy

The sample was exchanged twice with 99.80% $D_2O$ and redissolved in 99.99% $D_2O$. The NMR spectra of oligosaccharide were recorded from solutions in $D_2O$. The proton spectrum ($^1H$) and all two-dimensional spectra ($^1H$-$^1H$ COSY, $^1H$-$^1H$ TOCSY, ROESY, $^1H$-$^{13}C$ HMQC and $^1H$-$^{13}C$ HMBC) were recorded at 300 K with Bruker AMX 600 MHz spectrometer (operating frequencies 600.1 MHz for $^1H$ NMR and 160.9 MHz for $^{13}C$ NMR) and standard Bruker pulse programs were used in all experiments. Chemical shifts were reported relative to internal acetone ($\delta_H$ 2.225; $\delta_C$ 31.45) A mixing time of 100 ms for TOCSY was used. Two-dimensional spectra were obtained with 256 $t_1$ increments and 2048 datapoints along $t_2$. For homo- and heterocorrelation experiments respectively 32 and 128 scans were acquired for each $t_1$ value. Zero-filing was applied in the $t_1$ dimension and shifted squared sine bell or Gaussian functions were applied in both dimensions before Fourier transformation.

Sugar Analysis 1. hydrolysis—2 M TFA, 2 h, 121° C.;
2. reduction—Na ($BH_4$);
3. acetylation—100 μl pyridine and 100 μl $Ac_2O$, 30 min, 85° C.
4. GC analysis Absolute Configuration 1. methanolysis—oligasaccharide (~0.2 mg)+100 μl 2M HCl/MeOH, 16 h, 85° C.;
2. butanolysis—100 μl 2M HCl/BuOH, 16 h, 85° C.
3. acetylation—100 μl pyridine and 100 μl $Ac_2O$, 30 min, 85° C.
4. GC analysis Example 1

A number of different strains were screened in order to find a lactic acid bacterial strain capable of producing EPS. An overnight pre-culture was used to inoculate a fermentation chamber containing 200 ml of lactic growth medium (lactic 100b). The culture was incubated for 72 hours at 30° C. without stirring. The ability of each strain to produce EPS was tested at 24 and 72 hours. The results on FIG. 1 show that *Leuconostoc mesenteroides* 808-lactic strain at 24 hours produced approximately 28 g/l EPS and at 72 hours produced approximately 43 g/l EPS (see FIG. 1).

Further screening of different lactic acid microorganisms on sucrose agar showed that *Lactobacillus sake* spp., *Lactobacillus plantarum* spp. or *Lactobacillus salivarium* spp. were positive for EPS production (see below).

Example 2

In this example the cell number of EPS producing cells was evaluated. Thus, an overnight pre-culture of each lactic acid bacterial strain was used to inoculate a fermentation chamber containing 200 ml of lactic growth medium (lactic 100b). Each culture was then incubated for 72 hours at 30° C. without stirring. The results show that the lactic acid micro-organism *Leuconostoc mesenteroides* 808 strain is capable of maintaining cell numbers at 48 and 72 hour of fermentation higher than any of the other tested strains (see FIG. 2).

Example 3

The temperature at which *Leuconostoc mesenteroides* 808 strain produced optimum levels of EPS was tested. An overnight pre-culture of *Leuconostoc mesenteroides* 808 was used to inoculate four different fermentation chambers containing 200 ml of lactic growth medium (lactic 100b). After the inoculation, each fermentation chamber was incubated at 22° C., 25° C., 30° C. and 35° C. respectively without stirring. The pH at the start of the incubation was measured at a value of pH 7.4 and at the end of the fermentation period the pH was measured to be at a value of pH 4.1. The results presented in FIG. 3 show that *Leuconostoc mesenteroides* 808 strain produced maximum levels of EPS at 25° C.

Example 4

The production of EPS and the increase in viscosity was evaluated using *Leuconostoc mesenteroides* 808 strain. An overnight pre-culture of *Leuconostoc mesenteroides* 808 strain was used to inoculate a fermentation chamber containing 200 ml of lactic growth medium (lactic 100b). The culture was then incubated for up to 36 hours at 25° C. without stirring. The pH at the start of the incubation was measured at a value of pH 7.4 and at the end of the fermentation period the pH was measured to be at a value of pH 4.1. The results of this experiment are shown in FIG. 4.

Example 5

EPS production and viscosity increase as a function of a varied sucrose concentration using *Leuconostoc mesenteriodes* 808 strain were tested. An overnight pre-culture of *Leuconostoc mesenteroides* 808 strain was used to inoculate five different fermentation chambers containing 200 ml of lactic growth medium (lactic 100b) supplemented with 2%, 4%, 6%, 8% and 10% sucrose concentration respectively. The five different cultures were incubated for up to 72 hours without stirring. The pH at the start of the incubation in each chamber was measured at a value of pH 7.4 and at the end of the fermentation period the pH was measured to be at a value of pH 4.1. The results of this experiment show an increase in the EPS production (see FIG. 5A), and an increase in viscosity (see FIG. 5B), as functions of a varied sucrose concentration.

Example 6

Certain enzymes responsible for producing EPS can use maltose as an acceptor molecule which is in turn capable of controlling the chain length of the EPS sugar polymer formation and consequently the level of viscosity. Experiments were performed in order to ascertain the affect of maltose on EPS-chain length and viscosity using different *Leuconostoc mesenteroides* strains, as well as *Lactobacillus sake* spp., *Lactobacillus plantarum* spp. or *Lactobacillus salivarium* spp. One percent of an overnight pre-culture of different *Leuconostoc mesenteroides* strains grown in lactic growth medium was used to inoculate different fermentation chambers containing 200 ml of lactic growth medium supplemented with:

10% sucrose,
5% sucrose and 5% maltose (50/50 ration of sucrose/maltose)
7.5% sucrose and 2.5% maltose (75/25 ration of sucrose/maltose)

The cultures were incubated for up to 72 h without stirring and measurements for EPS production were taken at time points 24, 48 and 72 hours post-inoculation. The data presented on FIG. 6 shows that a significant amount of EPS is produced by the *Leuconostoc mesenteroides* 808 strain. The data also shows that the amount of EPS produced by *Leuconostoc mesenteroides* 808 can be modulated by the addition of varying amounts of maltose. Thus at 72 hours *Leuconostoc mesenteroides* 808 strain can produce approximately 36 g/L of EPS in a growth medium supplemented with 10% sucrose (FIG. 6). The graph of FIG. 6 also shows that the amount of EPS produced by *Leuconostoc mesenteroides* 808 was substantially reduced with the addition of varying amounts of maltose to the growth medium (FIG. 6).

The reduction in EPS production is likely due to the fact that maltose can induce the production of shorter polysaccharide chains. The reduction in the length of the polysaccharide chains can lead to an increase in fluidity i.e. reduction in viscosity. The results on FIG. 7 show that the viscosity of a growth medium containing 10% sucrose is greater than 4000 mPa which is dramatically reduced to 14 mPa in the medium containing a ratio of 75/25 sucrose/maltose and further reduced to 10 mPa at a ration of 50/50 Sucrose/Maltose. The results shown in FIG. 6 and FIG. 7 show that shorter, less viscous chains are formed with maltose as acceptor molecule which leads to a drop in EPS production and a drop in viscosity.

The effect of maltose on the ability of *Lactobacillus sake* 570 strain, *Lactobacillus plantarum* 853 strain or *Lactobacillus salivarium* 1502 strain to form EPS from sucrose, was tested (see FIG. 8, FIG. 9 and FIG. 10 respectively). The cultures were incubated for up to 48 h without stirring and measurements for EPS production were taken at time points 24 and 48 post-inoculation. The data presented on FIG. 8, FIG. 9 and FIG. 10 shows that a significant amount of EPS is produced from sucrose by the *Lactobacillus sake* 570 strain, *Lactobacillus plantarum* 853 strain or *Lactobacillus salivarium* 1502. The data also shows that the amount of EPS produced by *Lactobacillus sake* 570 strain, *Lactobacillus plantarum* 853 strain and *Lactobacillus salivarium* 1502 can be modulated by the addition of varying amounts of maltose. Thus at 24 hours *Lactobacillus sake* 570 strain can produce approximately 27 g/L of EPS in a growth medium supplemented with 10% sucrose (FIG. 8). The graph of FIG. 8 also shows that the amount of EPS produced by *Lactobacillus sake* 570 strain was substantially reduced with the addition of varying amounts of maltose to the growth medium (FIG. 8).

We also tested the capacity of *Leuconostoc mesenteroides* 808 strain, *Lactobacillus sake* 570 strain, *Lactobacillus plantarum* 853 strain and *Lactobacillus salivarium* 1502 strain to use lactose as a substrate for EPS production. Our results show that the enzymes produced by these lactic acid micro-organisms were also capable of polymerising lactose into EPS (see FIG. 11). The results on FIG. 11 show that the lactic acid bacteria that were tested were all capable of producing high amounts of EPS when incubated with lactose as an enzyme substrate. Thus, at 48 hours post inoculation *Leu-*

*conostoc mesenteroides* 808 strain produced 50 g/L EPS, *Lactobacillus sake* 570 strain produced 20 g/L EPS, *Lactobacillus plantarum* 853 strain produced 20 g/L EPS and *Lactobacillus salivarium* 1502 strain produced 20 g/L EPS. The results also demonstrate that the amount of EPS production when using lactose as a substrate can be modulated by varying the amount of maltose incorporated in the reaction.

Example 7

The effect of pH on EPS production by *Leuconostoc mesenteroides* 808 strain, *Lactobacillus sake* 570 strain and *Lactobacillus plantarum* 853 strain was tested. An overnight pre-culture of each one of the tested strains was used to inoculate a fermentation chamber containing 200 ml of lactic growth medium (lactic 100b). The cultures were then incubated for up to 48 hours at 25° C. without stirring. The production of EPS was tested at pH 6.5, pH 6.0 and pH 5.8. The results from these experiments are shown on FIG. 12, FIG. 13 and FIG. 14.

The highest EPS produced by *Leuconostoc mesenteroides* 808 strain was detected at pH 6.5 (see FIG. 12).

The highest EPS produced by *Lactobacillus sake* 570 strain was observed at pH 6.0 (see FIG. 13).

Example 8

The effect of pH on viscosity was also tested.

The highest viscosity for *Leuconostoc medenteroides* 808 strain was observed at pH 5.8 while the lowest viscosity for this strain was detected at pH 6.0 (see FIG. 15).

The highest viscosity for *Lactobacillus sake* 570 strain was observed at pH 6.5 with a reduction in the viscosity with the reduction of the pH conditions. Thus, the lowest viscosity for this strain was detected at pH 5.8 (see FIG. 16).

The highest viscosity for *Lactobacillus plantarum* 853 strain was observed at pH 6.0 (see FIG. 17).

Example 9

The structure of the an EPS derived oligomer produced by the *Lactobacillus sake* 570 was analysed using nuclear magnetic resonance analysis. The results are shown on FIG. 18 and demonstrate that the EPS back bone is formed of sugar molecules which are comprised of glucose molecules. The backbone of EPS is a α-1-6 linked Glucan (Dextran)

Example 10

The viability of *Leuconostoc mesenteroides* 808 strain in the presence of EPS was tested following spray drying. An overnight pre-culture of *Leuconostoc mesenteroides* 808 strain was used to inoculate a fermentation chamber containing 20 liters of lactic medium supplemented with 1% sucrose. The culture was then incubated for 72 hours without stirring. FIG. 19 shows the viability of *Leuconostoc mesenteroides* 808 strain before and after spray drying in the presence of 5% GLUCIDEX™, 10% GLUCIDEX™. and 10% skimmed milk. GLUCIDEX™ is a blend of nutritive saccharides, produced by controlled ensymatic hydrolysis which are routinely used in the food industry, particularly in milk fermentation products. GLUCIDEX™ can be used as a sweetening agent but preferably as a spray-drying saccharide rich syrup to improve the technical performance of the composition of the present invention, taste and cost effectiveness.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A composition for consumption, said composition comprising an isolated viable lactic acid micro-organism, an enzyme synthesised by said micro-organism and an exopolysaccharide (EPS) product of said enzyme; wherein said micro-organism is *Lactobacillus sakei* strain 570, and wherein said enzyme is glycosyl transferase enzyme, fructosyl transferase enzyme or glucan sucrase enzyme capable of polymerising sucrose and/or lactose and/or stacchyose, and/ or raffinose and/or verbascose.

2. A composition for consumption, said composition comprising an isolated viable lactic acid micro-organism, an enzyme synthesized by said micro-organism and an exopolysaccharide (EPS) product of said enzyme; wherein said micro-organism is *Lactobacillus sakei* strain 570 and wherein the EPS product is formed in situ by cultivating the lactic acid micro-organism with a suitable enzyme substrate, and wherein said enzyme is glycosyl transferase enzyme, fructosyl transferase enzyme or glucan sucrase enzyme capable of polymerising sucrose and/or lactose and/or stacchyose, and/or raffinose and/or verbascose.

3. A composition according to claim 1 or claim 2 wherein said EPS is a homo-EPS.

4. A composition according to claim 3 wherein said homo-EPS comprises an oligosaccharide component.

5. A composition according to claim 4 wherein said oligosaccharide component of the EPS comprises glucose.

6. A composition according to claim 1 or claim 2 wherein the polysaccharide or the oligosaccharide component of the EPS comprises fructan or glucan.

7. A composition according to claim 6 wherein the oligosaccharide is fructo-oligosaccharide or gluco-oligosaccharide.

8. A composition according to claim 1 or claim 2 wherein the amount of produced EPS is capable of being modulated.

9. A composition according to claim 8 wherein said amount of EPS is modulated by the number of viable lactic acid microorganisms, the length of the fermentation process, the incubation temperature, the pH or the acceptor molecule maltose.

10. A composition according to claim 1 or claim 2 wherein said EPS improves the texture, body, mouth feel, viscosity, structure and/or organoleptic properties of food product containing said EPS as an ingredient.

11. A composition according to claim 1 or claim 2 wherein the composition is used to ferment milk and produce a yoghurt like ingredient containing structure forming EPS and/or nutritional oligosaccharide.

12. A composition according to claim 1 or claim 2 wherein the composition acts as prebiotic when used as an ingredient to products for consumption or to pharmaceutical products.

13. A composition according to claim 1 or claim 2 wherein the components of the composition have the capacity to reduce the production of gas by the gastrointestinal microorganisms when used as ingredients to products for consumption or to pharmaceutical products.

14. A composition according to claim 1 or claim 2 wherein said composition is in a high concentrated form wherein the composition comprises a high concentration of the viable micro-organism and/or the enzyme synthesized by said micro-organism and/or the EPS produced by said enzyme.

15. A composition according to claim 1 or claim 2 wherein said composition is freeze dried, spray dried and/or resuspended.

16. A product for consumption obtained by a method comprising admixing a composition with another component so as to form said product for consumption; wherein said composition is a composition according to claim 1 or claim 2.

17. A product according to claim 16 wherein the composition is added to a dairy product.

18. A product according to claim 16 wherein the composition is added to yoghurt milk before and/or after the fermentation of said milk.

19. The product according to claim 16 wherein the product is a functional food.

20. A pharmaceutical product produced by a method comprising admixing a composition with another component to produce said pharmaceutical product, wherein said composition is a composition according to claim 1 or claim 2.

21. A container comprising a composition, wherein said composition is a composition according to claim 1 or claim 2.

22. A container comprising a composition, wherein said composition is a composition according to claim 1 or claim 2, and wherein said container has thereon a label indicating use and/or approval for use to improve the microbial balance of the gastrointestinal tract after consumption of said product.

23. A product according to 20 wherein the composition is added to a dairy product.

24. A product according to claim 17 wherein the composition is added to yoghurt milk.

25. A food product comprising as a food ingredient a composition according to claim 1 or claim 2.

26. A pharmaceutical product comprising a composition according to claim 1 or claim 2.

27. A composition according to claim 3 wherein said EPS comprises glucose.

* * * * *